United States Patent
Kumta et al.

(10) Patent No.: US 8,557,235 B2
(45) Date of Patent: Oct. 15, 2013

(54) BONE SUBSTITUTE COMPOSITIONS, METHODS OF PREPARATION AND CLINICAL APPLICATIONS

(71) Applicants: Prashant Nagesh Kumta, Pittsburgh, PA (US); Charles S. Sfeir, Pittsburgh, PA (US); Abhijit Roy, Pittsburgh, PA (US)

(72) Inventors: Prashant Nagesh Kumta, Pittsburgh, PA (US); Charles S. Sfeir, Pittsburgh, PA (US); Abhijit Roy, Pittsburgh, PA (US)

(73) Assignee: University of Pittsburgh—Of the Commonwealth System of Hihger Education, Pittsburgh, PA (US)

( * ) Notice: Subject to any disclaimer, the term of this patent is extended or adjusted under 35 U.S.C. 154(b) by 0 days.

(21) Appl. No.: 13/711,261

(22) Filed: Dec. 11, 2012

(65) Prior Publication Data

US 2013/0101676 A1   Apr. 25, 2013

Related U.S. Application Data

(62) Division of application No. 12/882,554, filed on Sep. 15, 2010, now Pat. No. 8,357,364.

(60) Provisional application No. 61/242,596, filed on Sep. 15, 2009.

(51) Int. Cl.
*A01N 63/00* (2006.01)
*A61K 9/14* (2006.01)
*C12N 5/00* (2006.01)

(52) U.S. Cl.
USPC .................. 424/93.7; 424/489; 435/325

(58) Field of Classification Search
USPC ............................ 424/93.7, 489; 435/325
See application file for complete search history.

(56) References Cited

U.S. PATENT DOCUMENTS

| | | | |
|---|---|---|---|
| 5,782,971 A * | 7/1998 | Constantz et al. | 106/690 |
| 7,247,288 B2 | 7/2007 | Kumta et al. | |
| 2006/0233851 A1 | 10/2006 | Simon et al. | |
| 2008/0095820 A1 | 4/2008 | Kumta et al. | |
| 2008/0160091 A1 | 7/2008 | Kropf et al. | |
| 2008/0226893 A1 | 9/2008 | Yang et al. | |

FOREIGN PATENT DOCUMENTS

| | | |
|---|---|---|
| EP | 2093256 A2 | 8/2009 |
| WO | WO2009009784 A1 | 1/2009 |

* cited by examiner

*Primary Examiner* — Karen Cochrane Carlson
*Assistant Examiner* — Natalie Moss
(74) *Attorney, Agent, or Firm* — Eckert Seamans Cherin & Mellott, LLC; Carol A. Marmo

(57) ABSTRACT

The present invention relates to bone substitute compositions and methods of their preparation, and their use in a wide variety of clinical applications. The compositions include calcium phosphate, acidic calcium salt, basic calcium salt, sodium hydrogen phosphate and porogen. The compositions further include a mixing liquid. The compositions can optionally include biological signaling molecules and/or a growth compound. Further, the compositions can optionally include a plasticizer.

14 Claims, 15 Drawing Sheets

US 8,557,235 B2

BONE SUBSTITUTE COMPOSITIONS, METHODS OF PREPARATION AND CLINICAL APPLICATIONS

This patent application claims the benefit of U.S. patent application Ser. No. 12/882,554 filed on Sep. 15, 2010, and entitled "Bone Substitute Compositions, Methods of Preparation and Clinical Applications", and U.S. Provisional Patent Application Ser. No. 61/242,596 filed on Sep. 15, 2009, and entitled "Nanostructured Injectable Bone Cement for Bone Regeneration".

GOVERNMENT CONTRACT

The research conducted for this invention was partially funded under grants (Nos. DAMD 17-02-1-0717, SAP-4100041556 and SAP-410045998) and a contract (No. DAMD 17-02-0717) from the government of the United States and therefore, the government of the United States has certain rights in this invention.

FIELD OF THE INVENTION

The present invention relates to bone substitute compositions, methods for their preparation, and their use in clinical applications. The compositions are particularly suitable for use in bone regeneration, bone tissue engineering and as a delivery vehicle for cellular and biological materials.

BACKGROUND OF THE INVENTION

Various polymer- and ceramic-based scaffolds have been studied for use as bone substitute compositions and for the purpose of bone regeneration. These scaffolds include hydroxyapatite (HA)-based ceramics and calcium phosphate cements (CPCs). CPCs are generally moldable, putty-like compounds that can be easily introduced into a defective bone site. They typically set within a period of time at normal body temperatures to form mechanically stable, osteo-conductive or osteo-inductive materials. Additionally, CPCs convert into natural bone-like calcium-deficient hydroxyapatite (CDHA) in vivo making them attractive for bone tissue engineering. Currently used CPCs have a relatively long setting time, for example, in excess of several tens of minutes, slow conversion, low resorption rates and low bone regeneration rates. CPCs would be more attractive for clinical applications if they exhibited enhanced resorption-degradation characteristics in vivo.

Further, the polymer and ceramic cement-based scaffolds that are known in the art for use as bone substitute compositions are generally not amenable for in situ incorporation of cells, growth factors and/or biological systems. This may be due, at least in part, to the harsh reaction conditions or reagents that are used and may be toxic to cells and biological systems. Hence, as a result, the cellular or biological components could be incorporated into the pre-fabricated system which would not allow one to substantially control the amount, distribution and homogeneity of the delivery agents. Further, the acidic or basic degradation products could also prove to be harmful to the cells or biological molecules added to the pre-fabricated system.

Reconstructive surgery in recent years has focused intensely on tissue repair and regeneration, in an attempt to overcome the limitations of the current treatment strategies. Artificial tissue substitutes have significantly assisted surgeons in the restoration of the form and, partly, the function of defective bones. In this context, the implementation of bioresorbable scaffolds have been regarded as an optimal model for tissue regeneration.

There is a need in the art to design and develop bone substitute compositions which can be generated under physiological conditions of neutral pH and may demonstrate the ability to contain nano-carriers of calcium phosphate that are complexed to cellular and/or biological materials, such as DNA, growth factors, cells and proteins. Additionally, it is desired for bone substitute compositions to have a reasonably short setting time, a reasonably rapid conversion time and relatively high resorption and bone regeneration rates.

Further, it is desired for bone substitute compositions to have relatively short initial setting times and relatively short final setting times; improved porosity of the CPCs, i.e. increased number and size of the pores inside the cement to accelerate bone tissue infiltration; increased exposed area to lead to greater resorption rates; and the ability to directly incorporate various cellular and/or biological materials in the developed apatitic-CPC to induce rapid bone regeneration around a defective bone site. Furthermore, it is desired that the incorporation of porosity, various cellular and/or biological materials including carriers of DNA, growth factors, proteins, and drugs, not impact the setting characteristics and mechanical properties of the bone substitute composition.

SUMMARY OF THE INVENTION

In one aspect, the present invention provides a bone substitute composition including a powder component and a liquid component. The powder component includes calcium phosphate, acidic calcium salt, basic calcium salt, material selected from monosodium hydrogen phosphate, disodium hydrogen phosphate and mixtures thereof, and porogen. The liquid component includes a colloidal mixture including nanoparticulate calcium phosphate and calcium salt. The bone substitute composition is effective to regenerate bone in the absence of a biological growth component.

The bone substitute composition can further include a plasticizer. The plasticizer can be present in the powder component of the bone substitute composition.

The calcium phosphate can be selected from the group of monocalcium monophosphate anhydrite, calcium hydrogenphosphate dihydrate, calcium hydrogenphosphate anhydrite, hydroxyapatite, alpha-tricalcium phosphate, beta-tricalcium phosphate, fluorapatite, octacalcium phosphate, tetracalcium phosphate, carbonated calcium phosphate, and mixtures thereof. The calcium phosphate can include alpha-tricalcium phosphate.

The acidic calcium salt is selected from the group of calcium sulfate, calcium hydrogenphosphate dihydrate, calcium hydrogenphosphate anhydrite, calcium oxalate, calcium citrate, calcium tartrate, calcium picrate and mixtures thereof.

The basic calcium salt is selected from the group of calcium carbonate, calcium bicarbonate, calcium dihydroxide, and mixtures thereof.

The porogen is selected from the group of recrystallized organic salt, recrystallized inorganic salt, engineered peptide, natural polymer, a composite of natural and synthetic polymers, synthetic biodegradable polymer, natural extra cellular matrix protein, and mixtures thereof.

The absence of the biological growth component in the composition can include the absence of BMP-2.

The composition can have a porosity of about 80 percent or greater.

In another aspect, the present invention provides a bone substitute composition including a powder component and a liquid component. The powder component includes calcium phosphate, acidic calcium salt, basic calcium salt, material selected from monosodium hydrogen phosphate, disodium hydrogen phosphate, and mixtures thereof, and porogen. The liquid component includes a colloidal mixture including nanoparticulate calcium phosphate and calcium salt. The porogen is present in an amount such that the composition has a porosity of about 80% or greater.

The composition can have a surface area of from about 60 $m^2$/gram to about 120 $m^2$/gm.

The composition can further comprise a plasticizer.

The composition can be osteo-inductive.

In yet another aspect, the present invention provides a method of preparing a bone substitute material. The method includes combining calcium phosphate, acidic calcium salt, basic calcium salt, material selected from monosodium hydrogen phosphate, disodium hydrogen phosphate and mixtures thereof, and porogen to form a powder component, and mixing the powder component with a liquid colloidal mixture including nanoparticulate calcium phosphate and calcium salt, the colloidal mixture being complexed with at least one of a compound selected from the group consisting of protein, peptide, DNA, drug, stem cell, normal cell, and combinations thereof. The bone substitute material is effective to regenerate bone in the absence of a biological growth component.

The bone substitute compositions described above can be used in clinical applications to repair or replace bone material.

BRIEF DESCRIPTION OF THE FIGURES

The invention as set forth in the claims will become more apparent from the following detailed description of certain preferred practices thereof illustrated, by way of example only, and the accompanying figures, wherein:

DETAILED DESCRIPTION OF THE INVENTION

Figure 1:
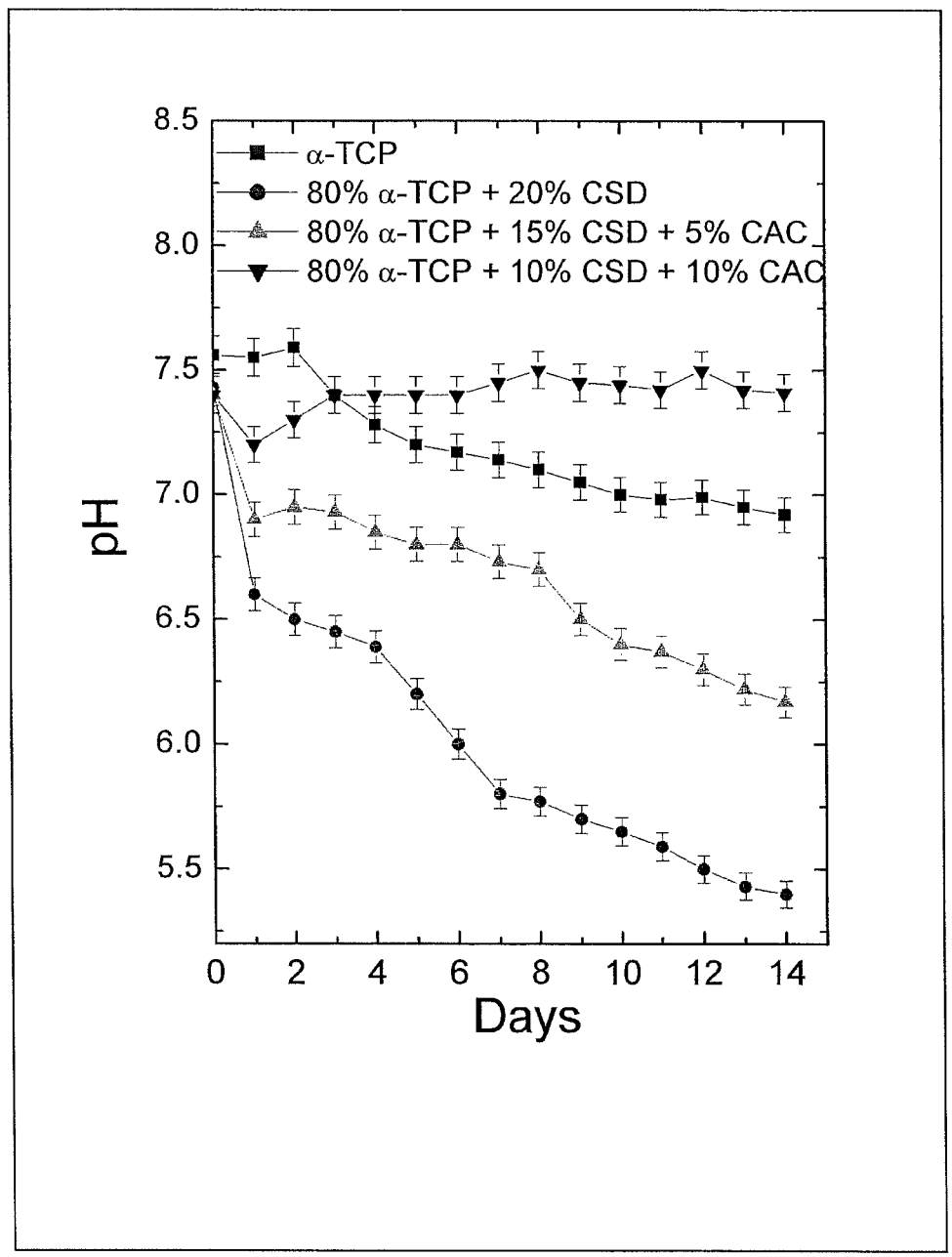
FIG. 1 is a plot showing the change of pH with time for various bone substitute compositions.

The present invention provides bone substitute compositions, methods for their preparation and their use in various clinical applications. The bone substitute compositions of the present invention are suitable for use in clinical applications to repair or replace defective native bone tissue. The defective native bone tissue can be in orthopedic, dental and craniofacial areas of a patient. The bone substitute compositions are effective to regenerate bone. Thus, the bone substitute compositions of the present invention are osteo-inductive. The bone substitute compositions are particularly suitable for use as a scaffold, for example, in a defective bone site. The bone substitute compositions can be in various forms, such as, but not limited to, paste, putty and cement. For example, the bone substitute compositions can be prepared in the form of a paste or putty and upon setting can form a cement. The physical characteristics of each of the paste, putty and cement can vary. The bone substitute compositions can be placed in vivo in a patient using various techniques known in the art, such as, by injecting or implanting the bone substitute composition into the patient. Further, the bone substitute compositions of the present invention may demonstrate advantageous characteristics, such as, but not limited to, excellent cell and host tissue biocompatibility. Furthermore, the bone substitute compositions of the present invention may demonstrate the above-mentioned advantageous characteristics in the absence of a biological growth component.

The bone substitute composition of the present invention includes a powder component and a liquid component. The powder component includes calcium phosphate, acidic calcium salt, basic calcium salt, material selected from monosodium hydrogen phosphate, disodium hydrogen phosphate or a mixture thereof, and porogen. The liquid component includes a mixing liquid.

The calcium phosphate can be selected from a variety of materials known in the art and includes, but is not limited to, monocalcium monophosphate anhydrite, calcium hydrogen phosphate dihydrate, calcium hydrogen phosphate anhydrite, hydroxyapatite, alpha-tricalcium phosphate, beta-tricalcium phosphate, fluorapatite, octacalcium phosphate, tetracalcium phosphate, carbonate calcium phosphate, and mixtures thereof. In one embodiment, the calcium phosphate includes alpha-tricalcium phosphate. The calcium phosphate can be present in the powder component of the bone substitute composition in varying amounts. It is contemplated that the amount of calcium phosphate employed may depend on the specific starting compounds selected for use in the powder component of the bone substitute composition of the present invention. In alternate embodiments, the calcium phosphate can be present in an amount of at least about 50% or no greater than about 98% by weight based on total weight of the powder component of the composition. In further embodiments, the calcium phosphate can be present in an amount such that it constitutes from about 50% to about 98%, or from about 60% to about 95%, or from about 65% to about 90% by weight based on total weight of the calcium phosphate, acidic calcium salt and basic calcium salt.

The acidic calcium salt can be selected from a variety of materials known in the art and includes, but is not limited to, calcium sulfate, calcium hydrogen phosphate dihydrate, calcium hydrogen phosphate anhydrite, calcium oxalate, calcium citrate, calcium tartrate, calcium picrate, and mixtures thereof. In one embodiment, the acidic calcium salt includes calcium sulfate. The acidic calcium salt can be present in the powder component of the bone substitute composition in varying amounts. It is contemplated that the amount of acidic calcium salt employed may depend on the specific starting compounds selected for use in the powder component of the bone substitute composition of the present invention. In alternate embodiments, the acidic calcium salt can be present in an amount of at least about 10% or no greater than about 20% or from about 10% to about 20%, by weight based on total weight of the calcium phosphate, acidic calcium salt and basic calcium salt.

The basic calcium salt can be selected from a variety of materials known in the art and includes, but is not limited to, calcium carbonate, calcium bicarbonate, calcium dihydroxide, and mixtures thereof. In one embodiment, the basic calcium salt includes calcium carbonate. The basic calcium salt can be present in the powder component of the bone substitute composition in varying amounts. It is contemplated that the amount of basic calcium salt employed may depend on the specific starting compounds selected for use in the powder component of the bone substitute composition of the present invention. In alternate embodiments, the basic calcium salt can be present in an amount of at least about 5% or no greater than about 20% or from about 5% to about 20%, by weight based on total weight of the calcium phosphate, acidic calcium salt and basic calcium salt.

The porogen can be selected from a variety of materials known in the art and includes, but is not limited to, recrystallized organic salt, recrystallized inorganic salt, engineered peptide, natural polymer, a composite of natural and synthetic polymers, synthetic biodegradable polymer, natural extra cellular matrix protein, and mixtures thereof. In one embodiment, the porogen is an inorganic salt, such as, but not limited to, potassium chloride, sodium chloride, sodium phosphate, sodium citrate, sodium tartrate, sodium acetate. In one embodiment, the porogen is a natural polymer, such as, but not limited to, mannitol, collagen, sucrose, fibrin, gelatin, alginate, chitosan, fibrin-gelatin composite, paraffin, polyol, poly lactic-co-glycolic acid (PLGA), and mixtures thereof. In another embodiment, the porogen is a synthetic biodegradable polymer, such as, but not limited to, poly-lactic acid, poly-e-caprolactone, poly-lactic-co-glycolic acid, and mixtures thereof. In yet another embodiment, the porogen is a natural extra cellular matrix protein, such as, but not limited to, urinary bladder matrix. The porogen can be present in the powder component of the bone substitute composition in varying amounts. It is contemplated that the amount of porogen employed may depend on the specific starting compounds selected for use in the powder component of the bone substitute composition of the present invention. In alternate embodiments, the porogen can be present in an amount of at least about 1% or no greater than about 60% by weight based on total weight of the total percentage of the calcium phosphate, acidic calcium salt and basic calcium salt, and the porogen. In further embodiments, the porogen can be present in an amount such that it constitutes from about 1% to about 60% or from about 10% to about 60% or from about 30% to about 50%, by weight based on total weight of the total percentage of the calcium phosphate, acidic calcium salt and basic calcium salt, and the porogen. In yet another embodiment, the porogen is present in an amount such that the bone substitute composition of the present invention has a porosity of about 80 percent or greater. Without intending to be bound by any particular theory, it is believed that rendering the bone substitute composition porous in the range of about 80 percent or greater, enables cells to penetrate the pores and uptake nanoparticulate carriers (which will be later described in detail) to produce an osteo-inductive composition.

The powder component of the bone substitute composition also includes monosodium hydrogen phosphate, disodium hydrogen phosphate, or mixtures thereof. The amount can vary and in one embodiment can be present such that the monosodium hydrogen phosphate, disodium hydrogen phosphate, or mixtures thereof, constitutes from about 5% to about 20% by weight based on total weight of the powder component.

In one embodiment, the powder component can optionally include calcium salt. Suitable examples can include those known in the art. Further, the amount of calcium salt can vary depending on the volume of the liquid component.

The mixing liquid in the liquid component of the bone substitute composition of the present invention includes a colloidal mixture including nanoparticulate calcium phosphate and calcium salt. The amount of nanoparticulate calcium phosphate present in the colloidal mixture can vary. Further, the amount of calcium salt in the colloidal mixture can also vary. The colloidal mixture including nanoparticulate calcium phosphate and calcium salt can be in the form of a solution. The solution can be prepared using a variety of known methods. In alternate embodiments, preparation of the solution can be in accordance with the procedure described in U.S. Pat. No. 7,247,288 and pending U.S. application Ser. No. 11/811,992 having Publication No. 2008/0095820 A1, which are both incorporated in their entirety by reference herein.

Furthermore, the pH of the colloidal mixture can vary. In alternate embodiments, the colloidal mixture can have a pH of from about 6.5 to about 9 or from about 7.2 to about 7.4. In one embodiment, the colloidal mixture is complexed to at least one cellular and/or biological compound which can include, but is not limited to, protein, peptide, DNA, drug, stem cell, normal cell and combinations thereof. The nanoparticulate calcium phosphate in the colloidal mixture can serve as carriers or delivery agents of these cellular and/or biological compounds.

Furthermore, the nanoparticulate calcium phosphate with the cellular and/or biological compounds complexed thereto can infiltrate the open pores of the bone substitute composition in vivo.

In one embodiment of the present invention, the bone substitute composition does not include a biological growth component, such as, but not limited to, biological signaling molecules and/or a growth compound. Thus, the bone substitute composition is prepared, formed into a bone substitute cement and employed in a clinical application, in the absence of a biological growth component, such as, but not limited to, BMP-2.

In an alternate embodiment of the present invention, the bone substitute composition includes a biological growth component, such as, but not limited to, biological signaling molecules and/or a growth compound. The biological growth component can be selected from a variety of biological growth components known in the art. A suitable biological growth component for use in the present invention includes, but is not limited to, BMP-2. The biological growth component can be in the form of a powder and can be included in the powder component of the bone substitute composition.

In one embodiment, calcium sulfate and calcium carbonate are present in the bone substitute composition in approximately equal amounts by weight. In a further embodiment, the calcium phosphate in the bone substitute composition constitutes at least about 50% by weight and the calcium sulfate and calcium carbonate are in approximately equal amounts by weight.

In still another embodiment, the bone substitute composition includes from about 75% to about 85% by weight of calcium phosphate, from about 8% to about 15% by weight of calcium sulfate, from about 8% to about 15% by weight of calcium carbonate, from about 5% to about 20% by weight of mono- or di-sodium hydrogen phosphate or a mixture thereof, based on total weight of these compounds, and the total composition (these compounds and porogen) being from about 30% to about 50% by weight porogen.

In one embodiment, wherein the powder component of the bone substitute composition includes calcium phosphate, acidic calcium salt, basic calcium salt, disodium hydrogen phosphate, and porogen, and the mixing liquid includes the use of a colloidal mixture including nanoparticulate calcium phosphate and calcium salt solution, the amount of the disodium hydrogen phosphate added to the powder component depends on the volume and composition of the colloidal mixture including nanoparticulate calcium phosphate and calcium salt solution in the liquid component. The stoichiometric amount of disodium hydrogen phosphate required to convert the excess $Ca^{2+}$ into hydroxyapatite can be calculated in accordance with the following equation:

$$(M_{Ca}) \times 10 \times Ca^{2+} + (M_{PO}) \times 6 \times HPO_4^{2-} + H_2O \rightarrow Ca_{10}(PO_4)_6(OH)_2$$

wherein $M_{Ca}$ is the molarity of the calcium ion (i.e. concentration of Ca ions in moles/liter in the colloidal mixture of nanoparticulate calcium phosphate solution) and $V_{Ca}$ is the volume of the colloidal mixture of nanoparticulate calcium phosphate solution used. $M_{PO}$ is the concentration of phosphate ions in moles/liter required to convert the certain volume and concentration of Ca-ions into hydroxyapatite. The value of $M_{PO}$ in grams is calculated in accordance with the following equation:

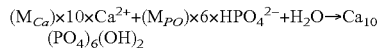

In addition to this amount ($M_{PO}$ in grams) of $Na_2HPO_4$, an excess (at least 0.25 molar) of $Na_2HPO_4$ is used to catalyze the bone substitute composition reaction. Thus, the minimum amount of $Na_2HPO_4$ required to add to the above mentioned bone substitute composition is ($M_{PO}$+0.25) moles for each liter of colloidal mixture of nanoparticulate calcium phosphate solution. Therefore, depending on the volume of colloidal mixture used for a specific bone substitute composition with a specific powder to liquid ratio, the amount of $Na_2HPO_4$ can be calculated. For example, a colloidal mixture of nanoparticulate calcium phosphate solution containing 0.2M $CaCl_2$ and colloidal nano-particles of hydroxyapatite to be used as a liquid in the above mentioned powder composition with a powder to liquid ratio of between 2.33 Wee and 1.51 g/cc, requires addition of between 10% and 20% $Na_2HPO_4$, respectively (by weight of the powder composition weight, i.e. powder composition to $Na_2HPO_4$ weight ratio is 10 to 5).

The powder component and the liquid component can be combined by simple mixing to form the bone substitute composition. Various known mixing techniques, methods and equipment can be used. In one embodiment, the components are combined at room temperature. Further, the order in which the various compounds in the powder component and the mixing liquid are combined with each other is not critical. The combination of the powder and liquid components will result in product having various forms, such as, for example, a paste or putty. The form of the product, and its physical characteristics, may depend on the amount of the powder component and the amount of the liquid component used. For example, a higher powder-to-liquid ratio can result in a dry paste and a lower powder-to-liquid ratio can result in a wet or liquid paste. The paste or putty product is allowed to set for a period of time and upon setting, the resultant product is in the form of a cement. Without intending to be bound by any particular theory, it is believed that the presence of calcium salt, e.g., in the powder component or the liquid component or both, assists in controlling the setting time of the resulting product. The cement product can then be implanted in vivo into a patient for use as a scaffold at a bone defect site.

In one embodiment, the ratio of powder component to liquid component is between about 1.50 g/ml:1.0 g/ml and 3.33 g/ml:1.0 g/ml. In this embodiment, the initial setting time is below about ten minutes or about seven minutes and the final setting time is below about 30 minutes or about 18 minutes. A higher ratio of powder component to liquid component (i.e., greater than 3.33 g/ml:1.0 g/ml) can result in a very dry paste having a setting time from about two to three minutes and therefore, may be difficult to handle for clinical applications. A lower ratio of powder component to liquid component (i.e., less than 1.50 g/ml:1.0 g/ml) can result in a very fluid paste which requires a significantly longer setting time.

In one embodiment, the resulting bone substitute composition is a moldable, putty-like structure that sets within minutes. In a further embodiment, the composition sets within less than ten minutes. In another embodiment, the setting time is from five minutes to twelve minutes.

In still another embodiment, the bone substitute composition can optionally include a plasticizer, e.g., a cohesion promoter. Without intending to be bound by any particular theory, it is believed that the presence of the plasticizer assists the particles to coalesce together to enable the coalesced particles to flow plastically. The plasticizer alters the surface chemistry of the particles and does not affect the setting characteristics of the bone substitute composition to form a cement. The plasticizer can be selected from a variety of materials known in the art and includes, but is not limited to, sodium dextran sulfate, alpha-cyclodextrin, beta-cyclodextrin, gamma-cyclodextrin, alginic acid, sodium salt, polyvinyl pyrrolidone, hyaluronic acid, potassium salt, chondroitin sulfate, chitosan lactate, hydroxypropyl methylcellulose, carboxymethyl cellulose and mixtures thereof. The plasticizer can be present in the powder component or in the liquid component or both. In a preferred embodiment, the plasticizer is present in the powder component. The plasticizer can be present in various amounts. It is contemplated that the amount of plasticizer employed may depend on the specific starting compounds selected for use in the bone substitute composition. In a further embodiment, the plasticizer can be present in an amount of from about 2% to about 10% by weight based on total weight of the powder component without the weight of porogen.

The presence of plasticizer can result in the bone substitute composition having a viscosity which renders it injectable into a bone, e.g., bone defect site, of a patient from about one to five minutes after initiating the mixing procedure of the powder and liquid components. After injection, the injectable composition sets and forms a cement in vivo, e.g., at the bone defect site within the patient.

In one embodiment, the resulting bone substitute composition, e.g., cement, of the present invention has an increased surface area as compared to the surface area of the starting powder component. For example, in one embodiment, the surface area of the resulting bone substitute cement is about sixty times the surface area of the starting powder component. In a further embodiment, the surface area of the resulting bone substitute cement is about 60 $m^2/g$ and the surface area of the starting powder component is about 1 $m^2/g$ or 2 $m^2/g$. The surface area can be further enhanced by subjecting the precursors to mechanical activation. In one embodiment, when mechanical activation is employed, the surface area of the starting powder component can increase to about 4 $m^2/g$ and the surface area of the resulting cement can increase to a range of about 90 to about 120 $m^2/g$. Thus, the bone substitute composition can have a surface area of from about 60 $m^2/g$ to about 120 $m^2/g$.

The bone substitute composition of the present invention can be used in bone engineering and bone regeneration applications. The bone substitute composition can be applied to a defective bone site using various techniques, methods and equipment known in the art. In alternate embodiments, the bone substitute composition can be implanted into a patient at the defective bone site using conventional surgical techniques known in the art, or the bone substitute composition can be injected into the defective bone site of the patient using conventional techniques including, but not limited to, a needle and syringe.

Without intending to be bound by any particular theory, it is believed that the significant increase in surface area of the resulting bone substitute cement as compared to the components thereof, is due, at least in part, to the reaction of the porogen (e.g., mannitol), acidic calcium salt (e.g., calcium sulfate dehydrate), and the basic calcium salt (e.g., calcium carbonate). The bone substitute compositions of the present invention have the ability to convert lower surface area starting materials to high surface area nano-crystalline calcium-deficient hydroxyapatite (CDHA). The nanostructured nature of the resulting CDHA formed due to the reaction and the high specific surface area, results in faster resorption kinetics of the bone substitute cement in-vivo compared to the resorption of in-vivo calcium phosphate cement in published data. The conversion into CDHA may also increase the adsorption amounts of proteins and other growth factors on the cement.

Furthermore, without intending to be bound by any particular theory, it is believed that the neutral pH, e.g., invariant pH, of the bone substitute composition of the present invention may contribute to an increased rate of bone regeneration. In the prior art, the acidic or basic bone substitute compositions caused transient cyto-toxicity which may adversely affect the adsorption of proteins and growth factors and therefore, may hinder bone regeneration.

Further, without intending to be bound by any particular theory, it is believed that incorporation of nanoparticulate calcium phosphate into the bone substitute composition is achievable without causing any significant change in the physical or chemical characteristics of the composition. The nanoparticulate calcium phosphate provides the ability to bind and condense cellular and biological compounds, such as DNA, growth factors and proteins, in addition to, adding these materials to the composition. Further, the use of a nanoparticulate calcium phosphate solution provides the ability to control the delivery of signaling molecules, anti-biotics, anti-bacterial agents, anti-fungal agents, growth factors and proteins. Moreover, the porosity of the bone substitute cement allows the nanoparticate calcium phosphate and the complexed cellular and biological material thereto, to be embedded within the open pores formed within the cement. The bone substitute cement includes the presence of macro-pores, micro-pores and meso-pores. The term "macro-pores" refers to pores having a size greater than about 15 nm; "micro-pores" refers to pores sized smaller than about 2 nm; and "meso-pores" refers to pores sized in the range of from about 2 to about 15 nm in size.

The following examples are merely provided for illustrative purposes and in no way are limiting upon the scope of the present invention.

EXAMPLES

Example 1

A powder composition was prepared which included 80% by weight of $\alpha$-$Ca_3(PO_4)_2$, 10% by weight of $CaSO_4.2H_2O$ and 10% by weight of $CaCO_3$. Thus, a 500.0 mg sample of the powder composition included 400 mg of $\alpha$-$Ca_3(PO_4)_2$, 50 mg of $CaSO_4$, $2H_2O$ and 50 mg of $CaCO_3$). A solution of 0.25M $Na_2HPO_4$ (pH=9.0) was used as a mixing liquid. The powder to liquid ratio was 2.33 gm/cc. The initial (workable time) and final (hardening) setting time of the bone substitute composition obtained at 298K using the above mentioned powder to liquid ratio was 7 minutes and 18 minutes, respectively. As referred to henceforth, this bone substitute composition is described as CSD-CPH.

Example 2

A powder composition was prepared which included 80% by weight of $\alpha$-$Ca_3(PO_4)_2$, 10% by weight of $CaSO_4.2H_2O$ and 10% by weight of $CaCO_3$. Thus, a 500.0 mg sample of the powder composition included 400 mg of $\alpha$-$Ca_3(PO_4)_2$, 50 mg of $CaSO_4$, $2H_2O$ and 50 mg of $CaCO_3$. 50 mg of $Na_2HPO_4$ anhydrous powder was mixed with this 500 mg of powder composition. A calcium phosphate particulate (CaP) solution based on 0.2M $CaCl_2$ was used as a mixing liquid. The powder to liquid ratio was 2.33 gm/cc. The initial (workable time) and final (hardening) setting time of the cement obtained at 298K using the above mentioned powder to liquid ratio was 7 minutes and 18 minutes, respectively. As referred to henceforth, this bone substitute composition is described as CSCC-CPH.

Example 3

A powder composition was prepared which included 80% by weight of $\alpha$-$Ca_3(PO_4)_2$, 10% by weight of $CaSO_4.2H_2O$ and 10% by weight of $CaCO_3$. Thus, a 300.0 mg sample of the powder composition included 240 mg of α-Ca$_3$(PO$_4$)$_2$, 30 mg of CaSO$_4$, 2H$_2$O and 30 mg of CaCO$_3$). 50 mg of Na$_2$HPO$_4$ anhydrous powder. Then, 200 mg of recrystallized mannitol were mixed with this 300 mg of powder composition. A nano-CaPs solution based on 0.2M CaCl$_2$ was used as a mixing liquid. The powder to liquid ratio was 2.33 gm/cc. The initial (workable time) and final (hardening) setting time of the cement obtained at 298K using the above mentioned powder to liquid ratio was 7 minutes and 18 minutes, respectively. As referred to henceforth, this bone substitute composition is described as PO-CPH.

Example 4

A powder composition was prepared which included 80% by weight of α-Ca$_3$(PO$_4$)$_2$, 10% by weight of CaSO$_4$.2H$_2$O and 10% by weight of CaCO$_3$. Thus, a 300.0 mg sample of the powder composition included 240 mg of α-Ca$_3$(PO$_4$)$_2$, 30 mg of CaSO$_4$, 2H$_2$O and 30 mg of CaCO$_3$. 50 mg of Na$_2$HPO$_4$ anhydrous powder. Then, 200 mg of recrystallized mannitol were mixed with this 300 mg of powder composition. To this 500 mg sample was added 15 mg of carboxymethyl cellulose (sodium salt) such that the weight percentage of the carboxymethyl cellulose was 3% based on the total weight of the 500 mg sample. A nano-CaP solution based on 0.2M CaCl$_2$ was used as a mixing liquid. The powder to liquid ratio was 2.10 gm/cc. The initial (workable time) and final (hardening) setting time of the cement obtained at 298K using the above mentioned powder to liquid ratio was 9 minutes and 50 minutes, respectively. The cohesion time for this cement paste was 3 minutes. The cement paste obtained by this method was injectable and the percentage injectability was greater than 90%. As referred to henceforth, this bone substitute composition is described as INJ-PO-CPH.

The crystalline phase evaluations and morphological characteristics of the INJ-PO-CPH cement was similar to the PO-CPH and all the results described below for PO-CPH are also valid and similar for the INJ-PO-CPH cement.

Compositions including (i) calcium phosphate alone, (ii) calcium phosphate and calcium sulfate, and (iii) calcium phosphate, calcium sulfate and calcium carbonate were prepared and tested to determine the pH of the compositions over time. The results are presented in FIG. 1. As shown in FIG. 1, the addition of calcium sulfate alone (e.g. 80% of α-Ca$_3$PO$_4$)$_2$ (α-TCP) and 20% of CaSO$_4$.2H$_2$O(CSD)) led to a decrease in pH over time, although there was not a significant pH change observed during the first 60 minutes of the reaction. The bone substitute compositions of the invention showed no appreciable change in pH over a period of two weeks.

The cement in accordance with the present invention CSCC-CPH (see Example-2) was converted fully into calcium deficient hydroxyapatite (CDHA) as found by measuring powder X-ray diffraction (XRD) and FTIR within 15 days of being when kept under Phosphate Buffered Saline (PBS) at 310K.

The surface was area measured using BET by adsorption of nitrogen of the CSCC-CPH powder composition and was found to be approximately 1.0 m$^2$/g. The surface area of the set cement (rod-shaped having of diameter of 6 mm and length of 15 mm) was measured following the final setting time which was approximately 26 m$^2$/g. The surface area was increased to approximately 55 m$^2$/g and to 35 m$^2$/g after being kept in PBS for 6 and 15 days, respectively, at 310K.

The macro-porosities inside the developed cement PO-CPH (see Example-3) were created using re-crystallized D-Mannitol (porogen) powder. All of the mannitol in the Mannitol-cement was leached out within 3 days when the pellet was kept under PBS at 310K. This was confirmed by measuring XRD and FTIR. The Mannitol-cement was found to be converted fully into CDHA as found by XRD after 6 days of being kept under PBS at 310K. The % porosity value obtained by density measurements for the cement containing 40% by weight of D-mannitol (Mannitol-cement) was found to be 75 (±5%) after the cement pellet was kept inside the phosphate buffer solution (PBS) for 6.0 days at 310K.

The presence of micro and macro-pores within the size range of 10 nm-300 μm for the PO-CPH cement after removal of mannitol were confirmed using Mercury-porosiometry and BET. The surface area of the Mannitol-Cement was measured following the final setting time and was found to be approximately 11 m$^2$/gm. The surface area had increased to approximately 59 m$^2$/g and to 42 m$^2$/g after being kept in PBS for 6 and 15 days, respectively, at 310K. This high surface area for the CSCC-CPH and PO-CPH provided the impetus for the conversion of the micron sized cement particles into nano-crystalline CDHA. This conversion of the micro size cement particles to nano-size CDHA was further confirmed using scanning electron microscope (SEM).

Example 5

A cement was developed (not of the invention) based on powders of α-TCP and Na$_2$HPO$_4$, comprising α-TCP particles of 7-21 μm in size. Initial and final setting time of this cement was found to be 7±1 min and 18±1 min., respectively, at 298K.

To incorporate micro, meso and macro-porosity into this cement, varying amounts of CSD were added to the cement. CSD is a relatively soluble calcium rich phase, and thus can be leached out from the cement to form pores. Further, it is contemplated that dissolved CSD in vivo should react with the phosphate ions present in body fluids to form apatite which could lead to the replacement of CSD crystals by pores and to the growth of neighboring apatite crystals.

The initial and final setting times of these cements (henceforth, described as CSD-CPH) containing varying amounts of CSD were found to be in the range of 9-7 (±1) min and 19-17 (±1) min respectively at 298K. The cohesion time of these cements were found to be ~4±1 min in phosphate buffer saline (PBS) and the injectability of these cements were observed to be in the range of 60-70%. CSD was used as the porogen in this example and 80% α-TCP and 20% CSD were used. The details of the protocol are described above in Example 2.

Figure 2:
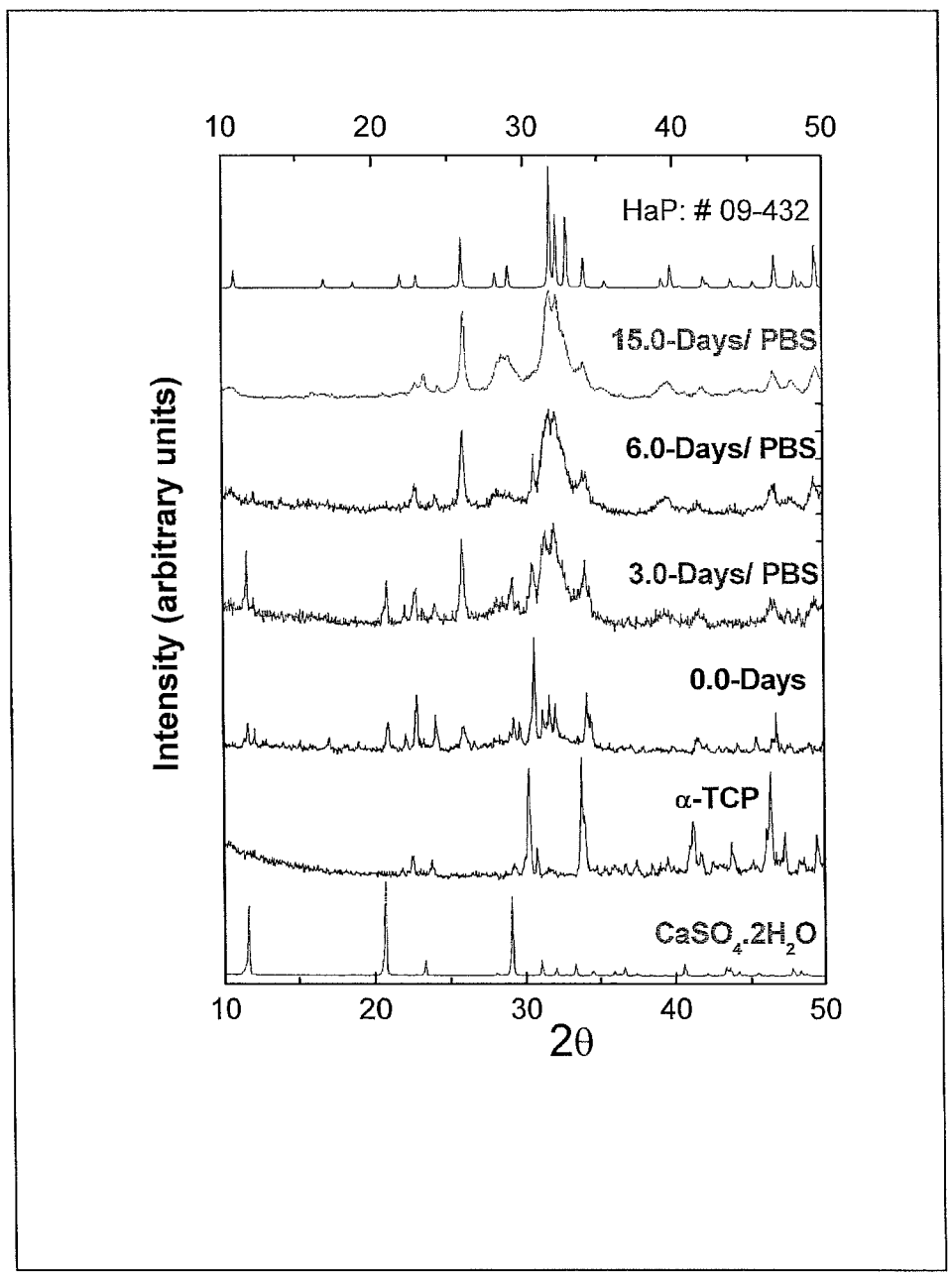
FIG. 2 is a plot showing x-ray diffraction patterns at various aging times for a bone substitute composition in accordance with an embodiment of the present invention.
Figures 3A, 3B, 3C:
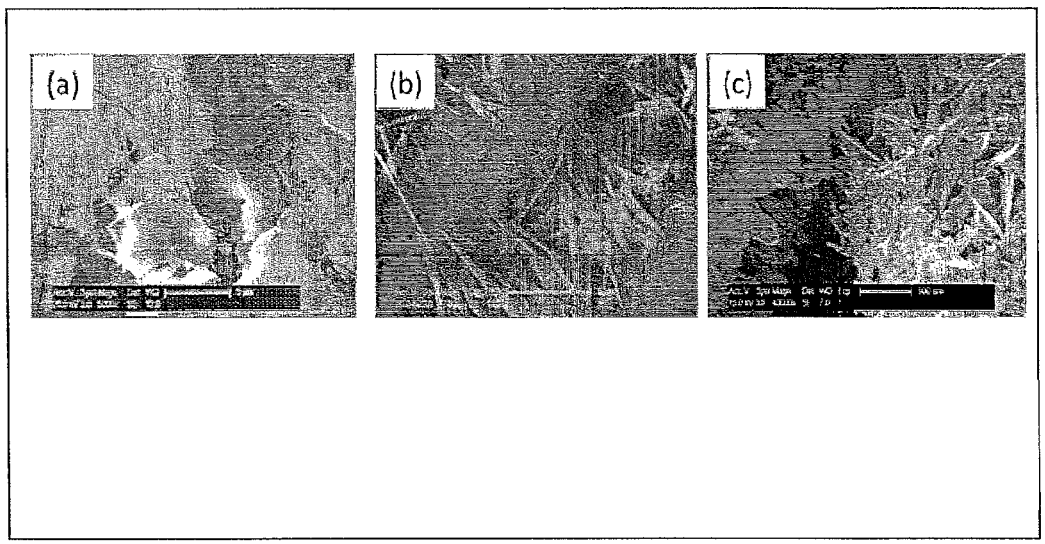
FIGS. 3(a), 3(b) and 3(c) are SEM images at various aging times for a bone substitute composition in accordance with an embodiment of the present invention.

Detailed studies of the crystalline phase and morphological evolution of these CSD-CPH cements with time in PBS were also conducted using X-ray diffraction (XRD) and scanning electron microscopy (SEM). XRD patterns, as shown in FIG. 2, reflect the conversion of the α-TCP phase into calcium deficient apatite (CDHA) and the dissolution of the CSD with time. XRD results clearly demonstrate that the α-TCP phase was converted fully into CDHA after 15.0 days. However, the CSD presented in the cement was completely dissolved in PBS and thus shows no characteristic peaks after 6.0 days. The SEM images (FIG. 3) show a change in morphology of the α-TCP particles and preferential growth of CDHA whiskers on the surface of the α-TCP particles. The cell viability test on the CSD containing cements showed cytotoxic effects of these cements compared to the CPH cements containing no-CSD. The cytotoxic effects of these cements were found to be due to the acidic nature of the cements (found by monitoring the pH changes of the solutions containing cements powders as shown in FIG. 1).

Figures 4A, 4B:
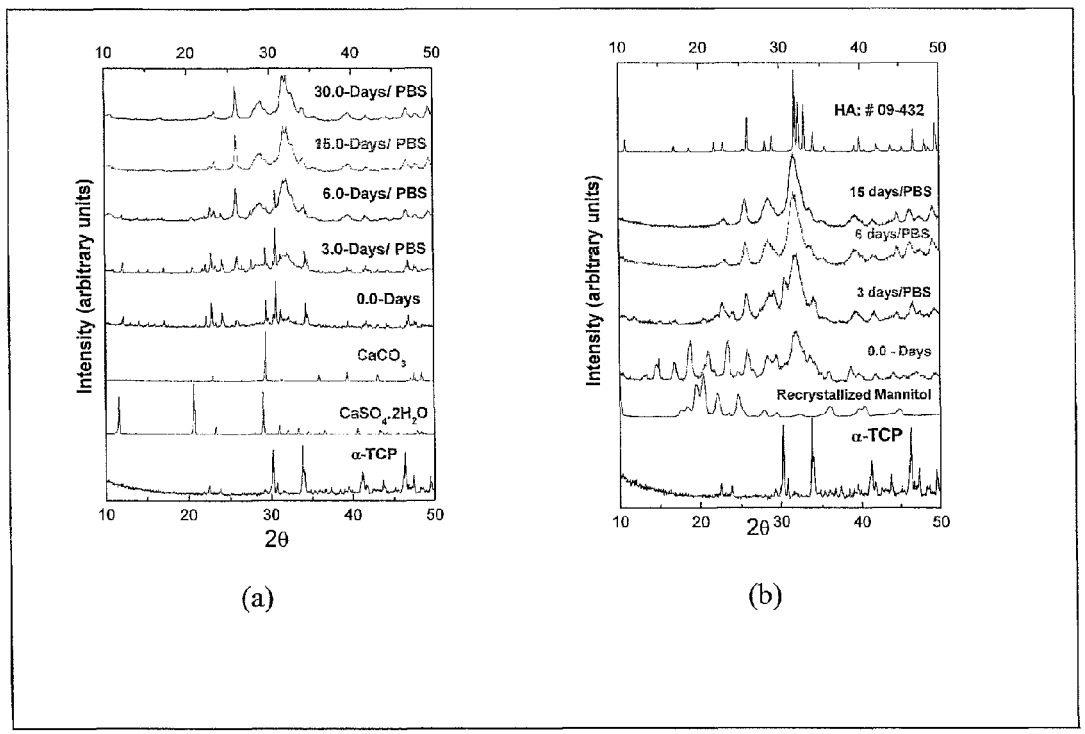
FIGS. 4(a) and 4(b) are plots showing x-ray diffraction patterns at various aging times for bone substitute compositions in accordance with embodiments of the present invention.
Figures 5A, 5B, 5C:
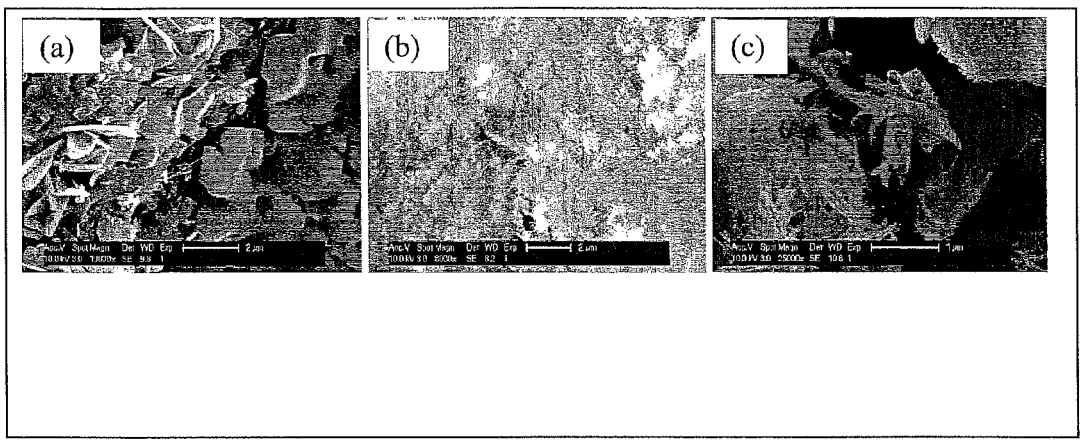
FIGS. 5(a), 5(b) and 5(c) are SEM images at various aging times for a bone substitute composition in accordance with an embodiment of the present invention.
Figures 6A, 6B, 6C, 6D:
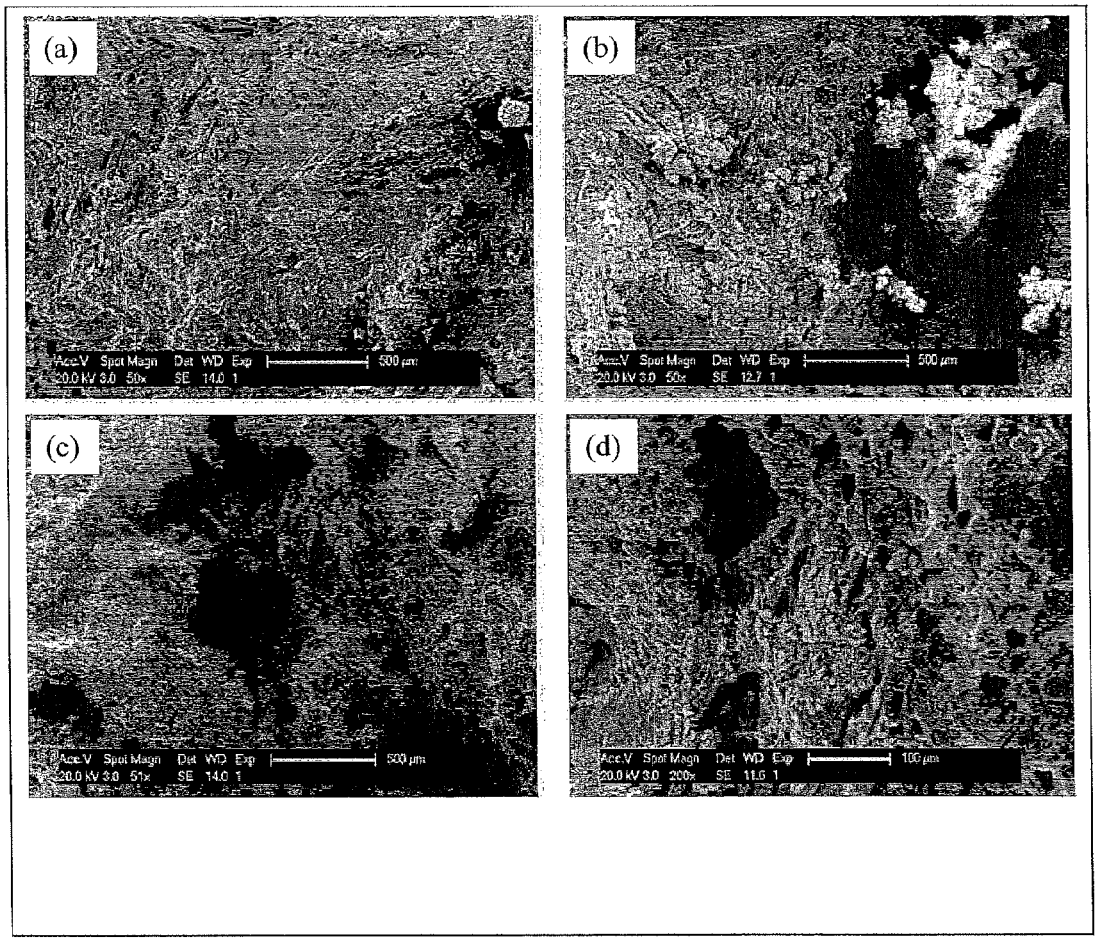
FIGS. 6(a), 6(b), 6(c) and 6(d) are SEM images at various aging times for a bone substitute composition in accordance with an embodiment of the present invention.

To avoid transient toxic effects of the acidic CSD-CPH cements in vivo, cements exhibiting neutral pH characteristics were developed. This was achieved by adding a controlled amount of basic calcium salt, CAC. 10% of CSD and 10% of CAC and 80% of α-TCP (see Example 2) were combined together. The setting characteristics of these CSCC-CPH cements were similar to the CSD-CPH cements described above. The phase evaluation of the CSCC-CPH cements kept under PBS showed that the complete conversion of the cements into CDHA occurred at approximately 15 days (see FIG. 4(a)). However, the morphology of the as-formed CDHA from these cements was found to be different from the CSD-CPH cements and the size (length and diameter) of the CDHA whiskers formed in case of the CSCC-CPH cements were in the nanometer range. See FIGS. 5(a), 5(b) and 5(c) which show SEM images of the CSCC-CPH cement at aging times in PBS at 310K of as-set, after 6 days and after 30 days, respectively. This result suggests that the CSCC-CPH cements may have a better in vivo resorption rate than CSD-CPH cements.

The in vivo resorption rate of cements was further improved by the introduction of controlled % porosity of micro-pores (to allow circulation of body fluid) and macro-pores (to provide a scaffold for blood-cell infiltration). It was contemplated that the micro-pores may facilitate cell attachment, migration and proliferation enabling good uptake of the carriers. This was achieved by using water soluble re-crystallized Mannitol (porogen). The introduction of 40% (by weight) of the porogen (into the PO-CPH cements) did not alter the initial and final setting times, cohesion time, and injectability characteristic of these cements (PO-CPH cements, see Example 3). The XRD patterns of porogen-containing cements showed that they were converted into CDHA within 6 days (see FIG. 4(b) which shows PO-CPH cements at varying aging times in PBS at 310K). The SEM images of the porogen-containing cements showed the formation of micro- and macro-pores after dissolution of the porogen (see FIGS. 6(a), 6(b), 6(c) and 6(d), which show the PO-CPH cement after aging times, in PBS at 310 K, of as-set, 1 day, 3 days and 6 days, respectively).

As used herein, the term "macro-pore" refers to pores having a size greater than 15 nm; "micro-pore" refers to pores sized smaller than 2 nm; and "meso-pore" refers to pores sized in between the two, i.e., between about 2-15 nm in size.

The pore size distribution and pore characteristic of the cements, with and without porogens were further studied using mercury-porosimetry, which demonstrated that the 40% Mannitol-containing PO-CPH cements contained large numbers of macro-pores (between 100 μm and 1 μm) compared to cements with no organic porogens, i.e. CSCC-CPH cements. However, both of these cements contained considerable numbers of micro-pores. A description of the surface area, apparent density, and percentage porosity of these cements are given in Table 1. The surface area data (Table1) together with the XRD results demonstrated that all the cements after 6.0 days of aging in PBS converted into nano-crystalline CDHA. The porosity values of these cements showed that the porogen-containing cements were highly porous containing both micro- and macro-pores. It was contemplated that high porosities of the porogen-containing cements together with the formation of nano-crystalline CDHA may improve the in vivo dissolution rate of these cements.

TABLE 1

The specific surface area was measured by $N_2$ adsorption (BET), the apparent density was measured using mercury porosiometry at 30.0 psi and the percentage porosity was measured for the different cements synthesized. $d_{HA} = 3.14$ g/cm$^3$ is the crystal density of hydroxyapatite and $d_{CPC}$ is the apparent density of a dried CPC.

| Samples | Surface area (m$^2$/g) | Apparent density (g/cc) at 24° C. | Porosity (%) = $[(d_{HA} - d_{CPC})/d_{HA}]$ X 100 |
|---|---|---|---|
| CSCC-CPH-cement-0.0 days in PBS | ~25.98 | ~1.15 | ~63 |
| CSCC-CPH-cement-6.0 days in PBS | ~55.01 | ~1.02 | ~67 |
| PO-CPH-cements-0.0 days in PBS | ~11.56 | ~1.12 | ~64 |
| PO-CPH-cements-6.0 days in PBS | ~59.03 | ~0.72 | ~77 |

Composition of the CSCC-CPH Cements 400 mg of α-Ca$_3$(PO$_4$)$_2$, 50 mg of CaSO$_4$.2H$_2$O and 50 mg of CaCO$_3$ was prepared. A 50 mg of Na$_2$HPO$_4$ anhydrous powder was mixed with this 500 mg of powder composition. A nano-CaPs solution based on 0.2M CaCl$_2$ was used as a mixing liquid. The powder to liquid ratio was 2.33 gm/cc.

Composition of the PO-CPH Cements 240 mg of α-Ca$_3$(PO$_4$)$_2$, 30 mg of CaSO$_4$.2H$_2$O and 30 mg of CaCO$_3$ was prepared. A 50 mg of Na$_2$HPO$_4$ anhydrous powder and 200 mg of recrystallized mannitol was mixed with this 300 mg of powder composition. A nano-CaPs solution based on 0.2M CaCl$_2$ was used as a mixing liquid. The powder to liquid ratio was 2.33 gm/cc.

Injectable Cement Formulation 336 mg of α-Ca$_3$(PO$_4$)$_2$, 42 mg of CaSO$_4$.2H$_2$O and 42 mg of CaCO$_3$ was prepared. A 70 mg of Na$_2$HPO$_4$ anhydrous powder and 280 mg of recrystallized mannitol was mixed with this 420 mg of powder composition. Furthermore, 21 mg of carboxymethyl cellulose was added and mixed with the cement-mannitol powder. A nano-CaPs solution based on 0.2M CaCl$_2$ was used as a mixing liquid. The cement powder and nano-CaPs solution were mixed with a powder to liquid ratio of 2.1 gm/cc. The results for this injectable formulation were similar to the results obtained for the cement formulations in Table 1.

In Vitro Experiments and Results

Figure 7A:
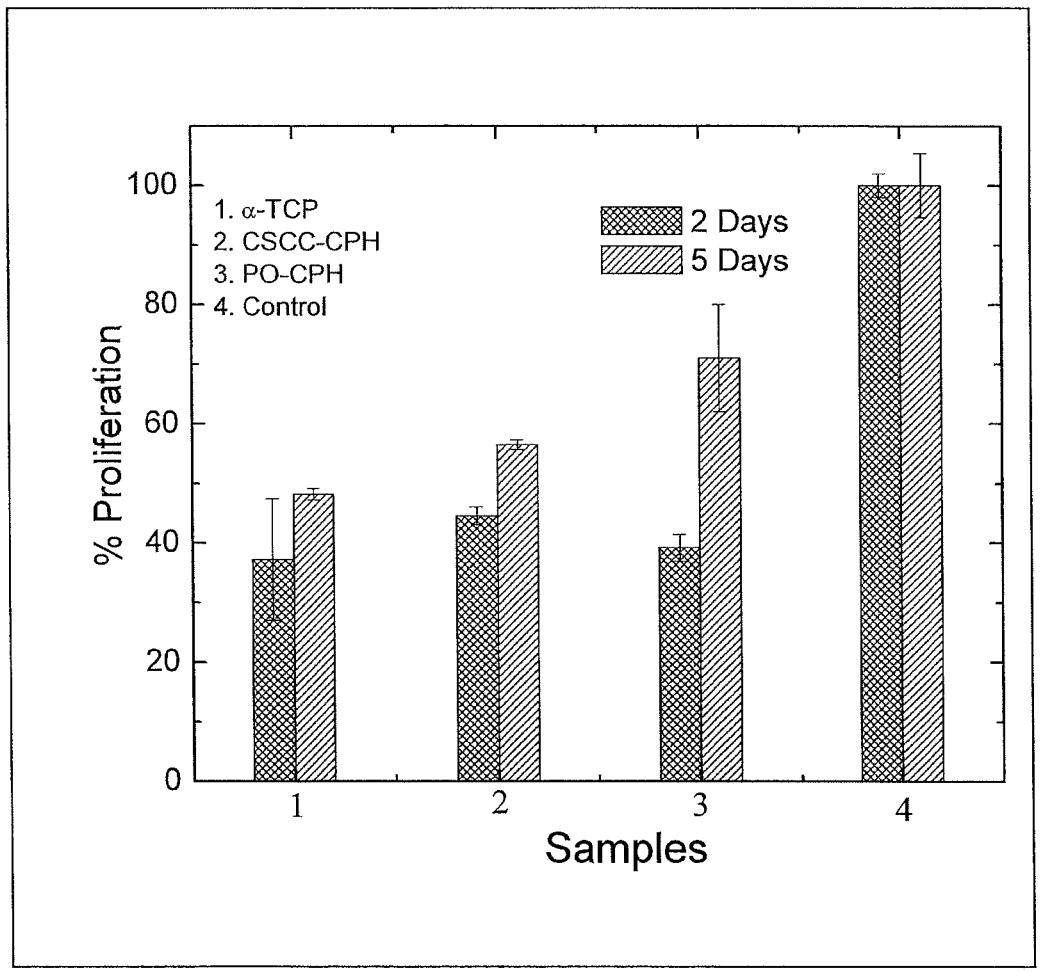
FIG. 7(a) is a bar graph showing cell proliferation on various bone substitute compositions including bone substitute compositions in accordance with embodiments of the present invention.

For all these cements MC3T3-cell proliferation was assessed with the nontoxic Alamar Blue dye and shown in FIG. 7(a). The proliferation results show that the cells grow well in all these cements, however, the Mannitol-cements showed the best cell growth compared to the other cements.

Bovine Serum Albumin (BSA) Release from Cement

The wells of a 96-well dish were coated with an inventive cement, or a commercial cement (Stryker HydroSet™), or contained no cement (tissue culture plastic (TCP)). The three substrates were coated with either a high or low concentration of fluorescently labeled bovine serum albumin (BSA). Solutions containing 0.8 or 0.33 mg/ml of BSA in PBS were prepared. Two hundred and fifty μl were added to the different substrates resulting in 0.20 and 0.0825 mg BSA/well for high and low BSA concentrations, respectively, with an n=3. The BSA solutions were left on the substrates for 2 days at 37° C. The wells were then rinsed for 1 minute with release medium containing α-MEM with 10% fetal bovine serum, 1% penicillin-streptomyocin, and 1% L-glutamine; the release medium was then refreshed. The release medium was removed from each well and the fluorescence was measured using a Perkin Elmer 1420 Victor$^3$V multilabel spectofluorometer after 1 and 4 hours and 1, 4, 7, 13, 21, 28, and 46 days. The cumulative BSA released was calculated by taking the sum of BSA measured from all time points.

Figure 7B:
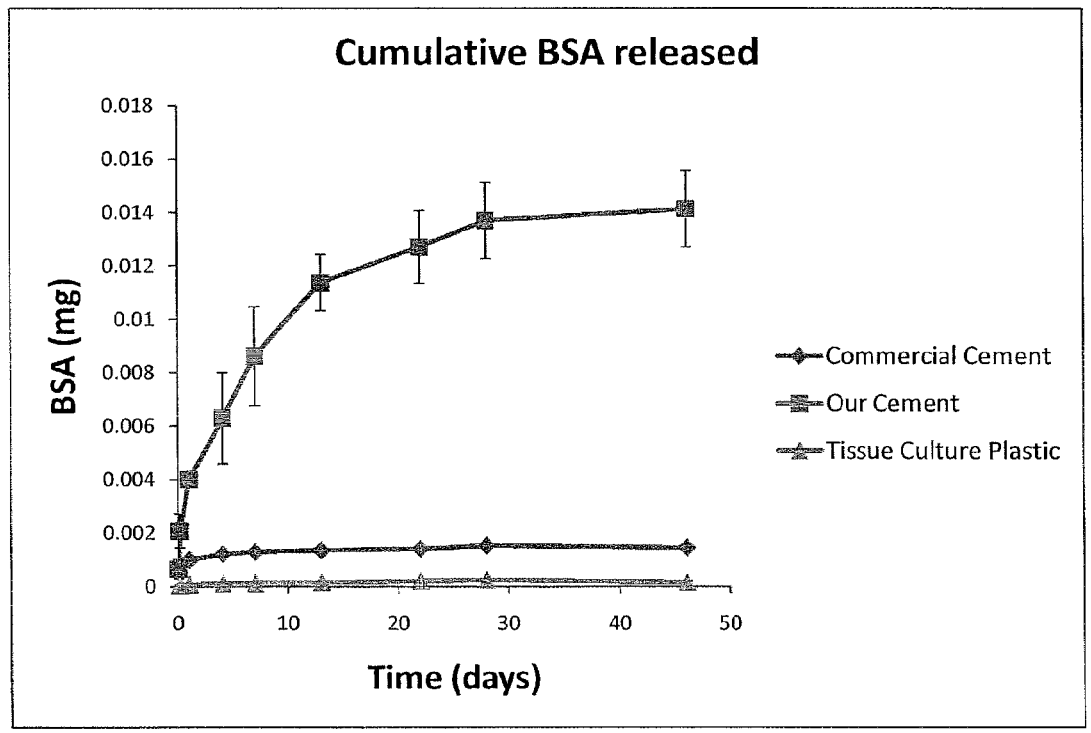
FIG. 7(b) is a plot showing a release profile of BSA from a bone substitute composition in accordance with an embodiment of the present invention.

FIG. 7(b) shows the release profile of BSA from the cement according to the present invention ("our cement"), the commercially available cement and the tissue culture plastic (TCP). The commercial cement and TCP adsorbed lower amounts of BSA in comparison to the inventive cement. The commercial cement and TCP cement showed an initial release at 1 and 4 hours whereas our cement showed a sustained release over a span of 46 days.

Figures 8A, 8B:
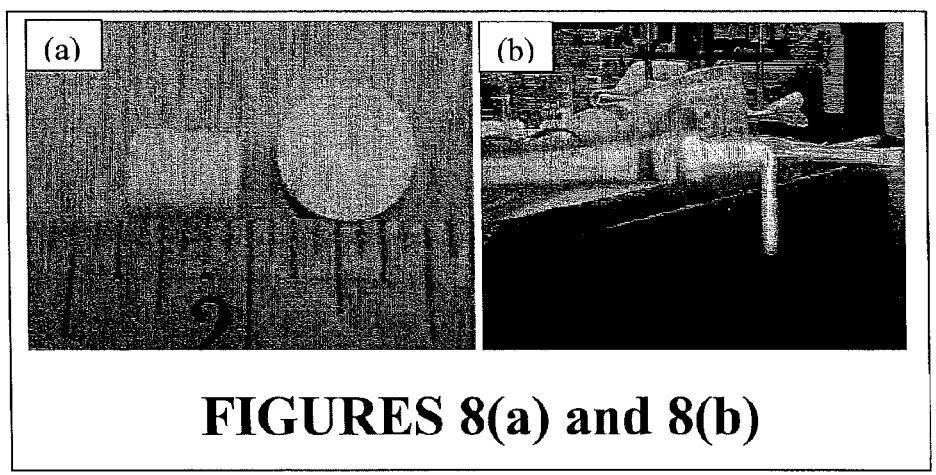
FIGS. 8(a) and (b) are digital images showing bone substitute compositions in accordance with embodiments of the present invention.

FIG. 8(a) shows a digital image of the as-prepared cement PO-CPH. As mentioned above, the cements can be synthesized in non-porous and porous forms. Furthermore, as shown in FIG. 8(b), the cement can be in the form an injectable paste.

3-D Printing of Cement

It was demonstrated to print scaffolds of arbitrary and complex 3D anatomical shapes with hierarchical porous structures mimicking the macroscopic and internal microstructure of organs and tissues while providing temporary mechanical function and mass transport properties using the developed cements.

Scaffolds were prepared for in vivo experiments (rather than using injectable cement). Scaffolds were printed (see FIG. 9) from CSCC-CPH powders generated using Example 2. A sample of 4.0 kilogram of CSCC-CPH powder was used in a 3-D printer (Z-corporation, Z-510) and distilled water was used as a binder and cement initiator. The printing of the scaffolds were carried out at 310K under laboratory conditions. The printed scaffolds were de-powdered and then immersed in PBS for 24 hrs at 310K. The scaffolds were then dried with acetone and sterilized using ethylene oxide for in vivo implantation.

In Vivo Experiments and Results

Methods

Scaffolds Preparation

PO-CPH Scaffolds 240 mg of α-$Ca_3(PO_4)_2$, 30 mg of $CaSO_4.2H_2O$ and 30 mg of $CaCO_3$ were mixed together. 50 mg of $Na_2HPO_4$ anhydrous powder and 200 mg of recrystallized mannitol was mixed with this 300 mg of powder composition. A nano-CaPs solution based on 0.2M $CaCl_2$ was used as a mixing liquid. The powder to liquid ratio was 2.2 μm/cc. The resulting cement paste was placed inside a Teflon mold to fabricate rod shaped samples. The cement paste inside the mold was kept at a temperature of 37° C. to harden for 120 minutes. The rod shaped cement scaffold was removed from the mold. The diameter and length of these PO-CPH scaffolds were 6 mm and 15 mm, respectively. The weights of these scaffolds were 650±20 mg. These scaffolds were sterilized using gamma-irradiation before implantation.

BMP-2 Loaded PO-CPH Scaffolds

The rod shaped PO-CPH scaffolds were prepared and sterilized using gamma-irradiation. The nano-Caps loaded with BMP-2 was prepared by mixing 47 μL of BMP-2 (concentration 1.5 mg/mL) with 4.65 μL of 4M $CaCl_2$. This mixture was then added to 75 μL of 1.91 mM phosphate buffer to form the BMP-2 loaded nano-CaPs. The final volume of the BMP-2-containing nano-CaPs solution was 126.65 μL. All of the liquids used in this method were sterilized prior to use and were handled under sterilized conditions during mixing and handling. This 126.65 μL solution was carefully soaked into the dry sterilized preformed PO-CPH cement scaffolds and stored at 4° C. The total BMP-2 loading was 70 μg/scaffold. In the case of the 3-D printed structures, the same procedure was used except that the BMP-2 loading was tested at 70 μg and also reduced to 35 μg/scaffold.

INJ-PO-CPH Paste for Craniofacial Critical Size Defects 336 mg of α-$Ca_3(PO_4)_2$, 42 mg of $CaSO_4.2H_2O$ and 42 mg of $CaCO_3$ were prepared. 70 mg of $Na_2HPO_4$ anhydrous powder and 280 mg of recrystallized mannitol were mixed with this 420 mg of powder composition. Furthermore, 21 mg of carboxymethyl cellulose was added and mixed with the cement-mannitol powder. A nano-CaPs solution based on 0.2M $CaCl_2$ was used as a mixing liquid. This powder mixture was sterilized using ethylene oxide before implantation. All the liquids were sterilized using filtration before the preparation of nano-CaPs. The cement powder and nano-CaPs solution were mixed with a powder to liquid ratio of 2.1 gm/cc under sterilized conditions in the surgery room and the paste was used to fill a craniofacial critical size defect.

BMP-2 Loaded INJ-PO-CPH Paste for Craniofacial Critical Size Defects 336 mg of α-$Ca_3(PO_4)_2$, 42 mg of $CaSO_4.2H_2O$ and 42 mg of $CaCO_3$ were prepared. 70 mg of $Na_2HPO_4$ anhydrous powder and 280 mg of recrystallized mannitol were mixed with this 420 mg of powder composition. Furthermore, 21 mg of carboxymethyl cellulose was added and mixed with the cement-mannitol powder. A nano-CaPs solution based on 0.2M $CaCl_2$ was used as a mixing liquid. This powder mixture was sterilized using ethylene oxide before implantation. All the liquids were sterilized using filtration before the preparation of nano-CaPs. During nano-CaPs preparation, BMP-2 was added to the $CaCl_2$ and this solution was added dropwise to phosphate buffer solution. The cement powder and BMP-2-containing nano-CaPs solution were mixed with a powder to liquid ratio of 2.1 gm/cc (Similar to Example-4) under sterilized conditions in the surgery room and the paste was used to fill a craniofacial critical size defect.

Surgical Technique

1. Rabbit Ulna Critical Size Defect

Twelve skeletally mature adult New Zealand White rabbits (~kg 3.200) were used. Following induction to general anesthesia, a 4 cm length anterolateral incision was made over the left forelimb and the tissue overlying the diaphysis of the ulna was dissected. A critically sized defect was created in the ulna of each rabbit forelimb by removing 15 mm of midshaft diaphyseal bone. In the osteotomy space, different types of scaffolds were implanted: Group 1: CaP cement alone; and Group 2: CaP cement+BMP-2. The soft tissues were approximated with interrupted 4-0 Vicryl (Ethicon, Somerville, N.J.) and the skin was closed with 3-0 monofilament non-absorbable sutures (Ethilon). All animals received 0.02 mg/kg of Ketoprophine (SQ), every 8-12 hours for 3 days postop for analgesic purposes and postoperative SQ injections (2 mg/kg) of Baytril (Bayer Corp., Shawnee Mission, Kans. 66201) BID for 3 days prophylaxis for infection. Eight weeks following surgery, all the rabbits were euthanatized. The forelimbs were removed, stripped of soft tissues, and prepared for analyses.

2. Craniofacial Critical Size Defect

All rabbits were anesthetized with an IM injection (0.59 ml/kg) of a solution of 91% Ketaset (Ketamine Hydrochloride, 100 mg/ml) and 9% Rompun (Xylazine, 20 mg/ml). The scalps were then shaved, depilated, scrubbed with povidine/alcohol, and prepared for sterile surgery. The calvaria were exposed using a midline scalp incision and the skin reflected laterally to the supraorbital borders. Holes were then made in the periosteum and bone using a fine dental burr (0.4 mm) Then, the holes were connected and the skull was extirpated and removed in one piece, approximately 15 $mm^2$ critical size defect (CSD) was made by using a dental cutting burr and hand engine. The dura mater was left in situ.

The scaffolds were made under sterile conditions and put into the defect area. The scalp wounds were closed with 4.0 ethilon sutures. All animals received 0.02 mg/kg of Buprenorphine (SQ), every 8-12 hours for 3 days post-op for analgesic purposes. In addition, all animals received postoperative SQ injections (2 mg/kg) of Baytril (Bayer Corp., Shawnee Mission, Kans. 66201) BID for 5 days prophylaxis for infection. Skin sutures were removed at 10 days post-operatively.

Body weight, bony defect healing, and cranial vault growth were assessed and monitored at 0, 2, 4, and 6 weeks postoperatively by using serial head radiographs. At 8 weeks postoperative, all rabbits were anesthetized with an IM injection of a solution of ketimine (40 mg/kg) and xylazine (7 mg/kg) and euthanized with an IV (300 mg/kg) injection of pentobarbital (Nembutal, Abbott Laboratories, North Chicago, Ill.). The CSDs were harvested for microCT analysis and histological assessment.

3. Subcutaneous Cement Implantation

Adult mice (aged 8-10 weeks) were utilized. The mice were anesthesized using Isofluran 2-5%; Ketamine 80-100 mg/kg and Xylazine 2 mg/kg IP were also used if deemed necessary. The effect of the anesthetic was determined by absent whisker-twitch response and unresponsiveness to gentle, passive extremity extension. Ophthalmic ointment was gently placed on the corneas. The surgical site was shaved with an electric clipper, prepped with betadine and draped in standard aseptic fashion. The mice were then numbered using a base three ear notch system.

The operating field was disinfected with 5% solution of iodine. A 1 to 2 cm incision on the back of the mice was made and the bone cement implants were placed into a subcutaneous pocket created in the dorsal area. The wound was closed with skin staples or sutures (the sutures were removed on day 7-9). Each animal received 2 or 4 implants.

Imaging Assessment

Animals were followed-up at regular intervals of 2, 4, and 8 weeks postoperatively with radiographs. At 8 weeks computed tomography (CT) using a Scanco Medical AG μCT 40 system followed by histological assessment were carried out. The percentage areas of the ulnar critical sized bone defect occupied by newly formed bone were calculated.

Following euthanasia the explanted forelimbs were scanned. The new bone formation was analyzed by extracting the region of new bone in the critical size defect using semi-automated contouring.

Non-parametric tests were used and the significant level was considered at $p<0.05$.

Histological Assessment and Histomorphometry

Following micro CT scan, the harvested specimens were fixed with 2% paraformaldehyde, decalcified, dehydrated through a graded series of alcohols and embedded in paraffin using standard tissue processor schedule. Approximately 15 serial sections through the center of the defect were cut at a thickness of 4-6 micrometers. Histological sections were stained by either Hematoxylin and Eosin (H&E) or Masson's Trichrome and examined using a Nikon TE2000 photomicroscope. Quantitative assessments was achieved using an acquisition, and measurement of newly formed bone bridge (matrix and cells). These images were analyzed using the Bioquant Osteo image analysis software specifically identifying areas of the tissues, e.g. those mineralized and those not mineralized. A determination of nominal values for histomorphometric assessments were accomplished to define the minimal number of fields and sections to assess. A standardized level of magnification were used for all analyses and a standard number of microscopic fields and sections were examined for each experimental cohort at each time. Morphological features within the defect were identified and enhanced using computerized software in an identical manner for all experimental replicates. The morphological aspects were quantified (bone/mm$^2$) using a Nikon TE2000 photomicroscope fitted with a color digital camera (Qimaging) and integrated with an image analysis system (Bioquant Osteo). Ten percent of the specimens were scanned and measured twice for inter-rater reliability.

Results

Materials and In-Vitro Characterization

The calcium phosphate cements were fabricated under neutral pH conditions with the direct incorporation of nano-structured calcium phosphates (NanoCaPs) as delivery agents for growth factors and proteins such as BMP-2. The cements all showed the formation of nano-structured hydroxyapatite (HA) as the primary phase after immersion in PBS indicating the probable phase that would likely form in vivo. The cements also showed excellent cell attachment and cellular migration results indicating their strong biocompatibility. The formation of nano-structured HA and the resulting higher specific surface area were added indications of the likely faster resorption kinetics of the cement when implanted.

All animals from all the groups wherein scaffolds were implanted, survived until the day of euthanasia. There were no complications encountered in terms of local or systemic adverse effects with regard to the implantation of the scaffolds.

Ulnae Critical Size Defect Results

The results showed that the bone substitute composition prepared in accordance with the present invention (in the absence of BMP-2) had the ability to regenerate an ulnae critical size bone defect. When BMP-2 was added to the bone substitute composition, increased bone regeneration was observed and faster cement resorption was achieved as compared to the bone substitute composition without the presence of BMP-2. Both cements with and without BMP-2, yielded higher regeneration potential than the control sample of an organic matrix without the BMP-2. The discussion below details the radiographic, micro-CT and histological assessment of the bone regenerative strategy that was employed using the moldable porous calcium phosphate (CaP)-based cements and its results.

Craniofacial Critical Size Defect Results

The results showed that the bone substitute composition prepared in accordance with the present invention (in the absence of BMP-2) had the ability to regenerate a calvarial critical size bone defect. When BMP-2 was added to the bone substitute composition, increased bone regeneration was observed and faster cement resorption was achieved compared to the bone substitute composition without the presence of BMP-2. Both cements, with and without BMP-2, yielded higher regeneration potential than the control of organic matrix without BMP-2. The discussion below details the radiographic, micro-CT and histological assessment of the bone regenerative strategy that was employed using the moldable porous CaP-based cements and its results.

Subcutaneous Cement Implantation Results

Figure 14:
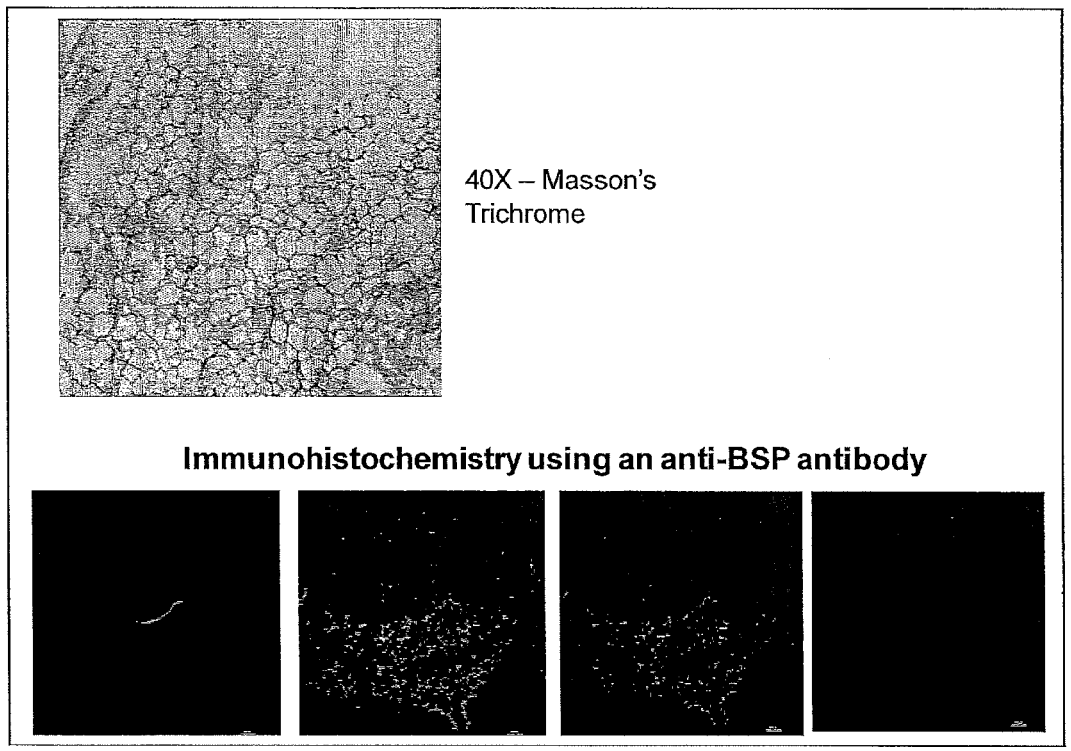
FIG. 14 is a histological assessment for an implant of a bone substitute composition in accordance with an embodiment of the present invention.

The data showed that the biocompatible porous cement was infiltrated by cells from the adjacent wound area. These cells, upon their interaction with the cement, appeared to start differentiating into bone cells as shown by the deposition of an organic matrix that contained extracellular matrix bone proteins such as bone sialoproteins (BSP) (FIG. 14). This data provided support for the osteo-inductivity characteristic of the cement to induce cells to differentiate towards the bone lineage.

Cement Results

Figures 10A, 10B, 10C:
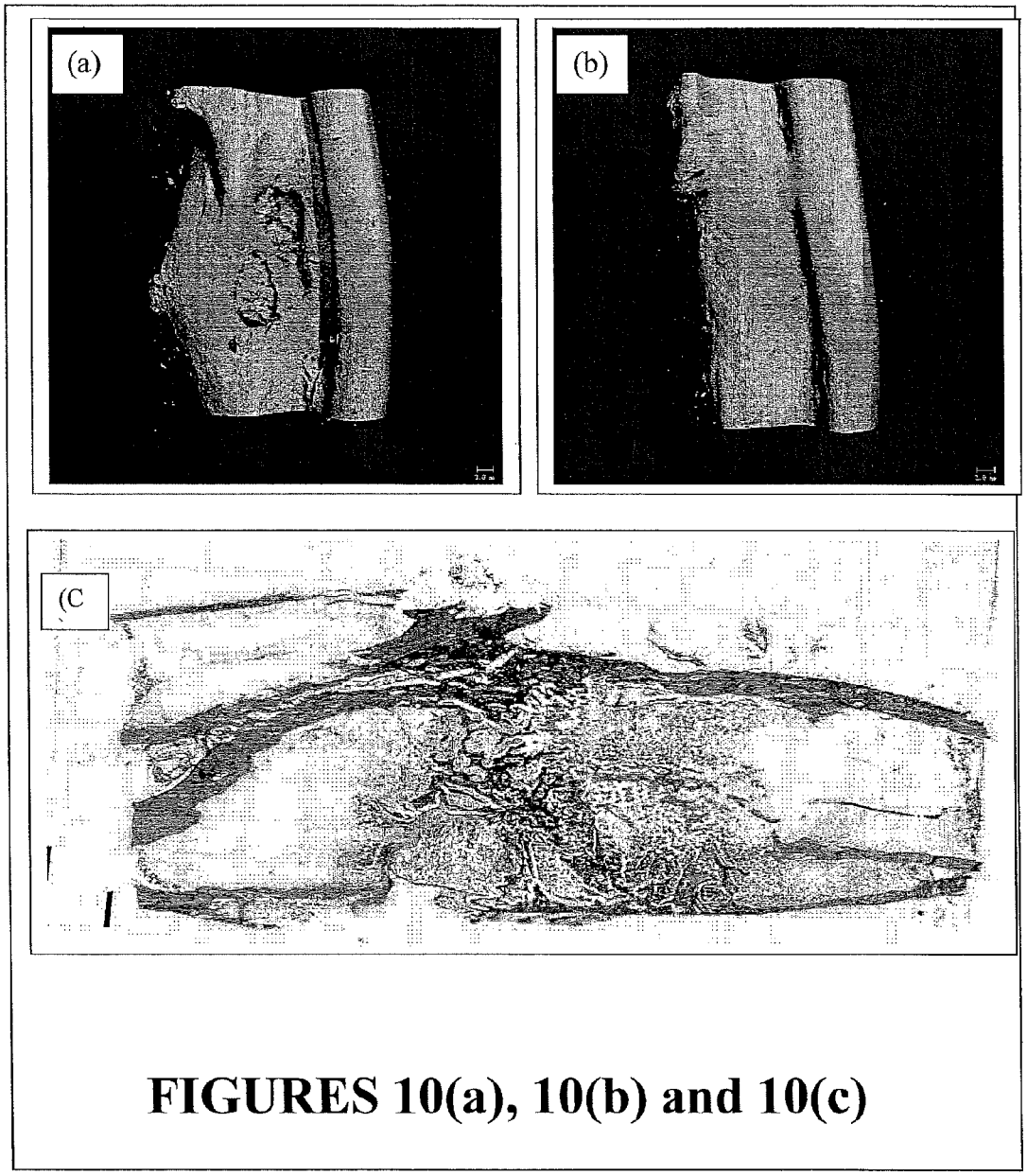
FIGS. 10(a) and 10(b) are micro-CT images of an implanted bone substitute composition in accordance with an embodiment of the present invention.
FIG. 10(c) is a histological assessment showing new bone formation for a bone substitute composition in accordance with an embodiment of the present invention.
Figure 13:
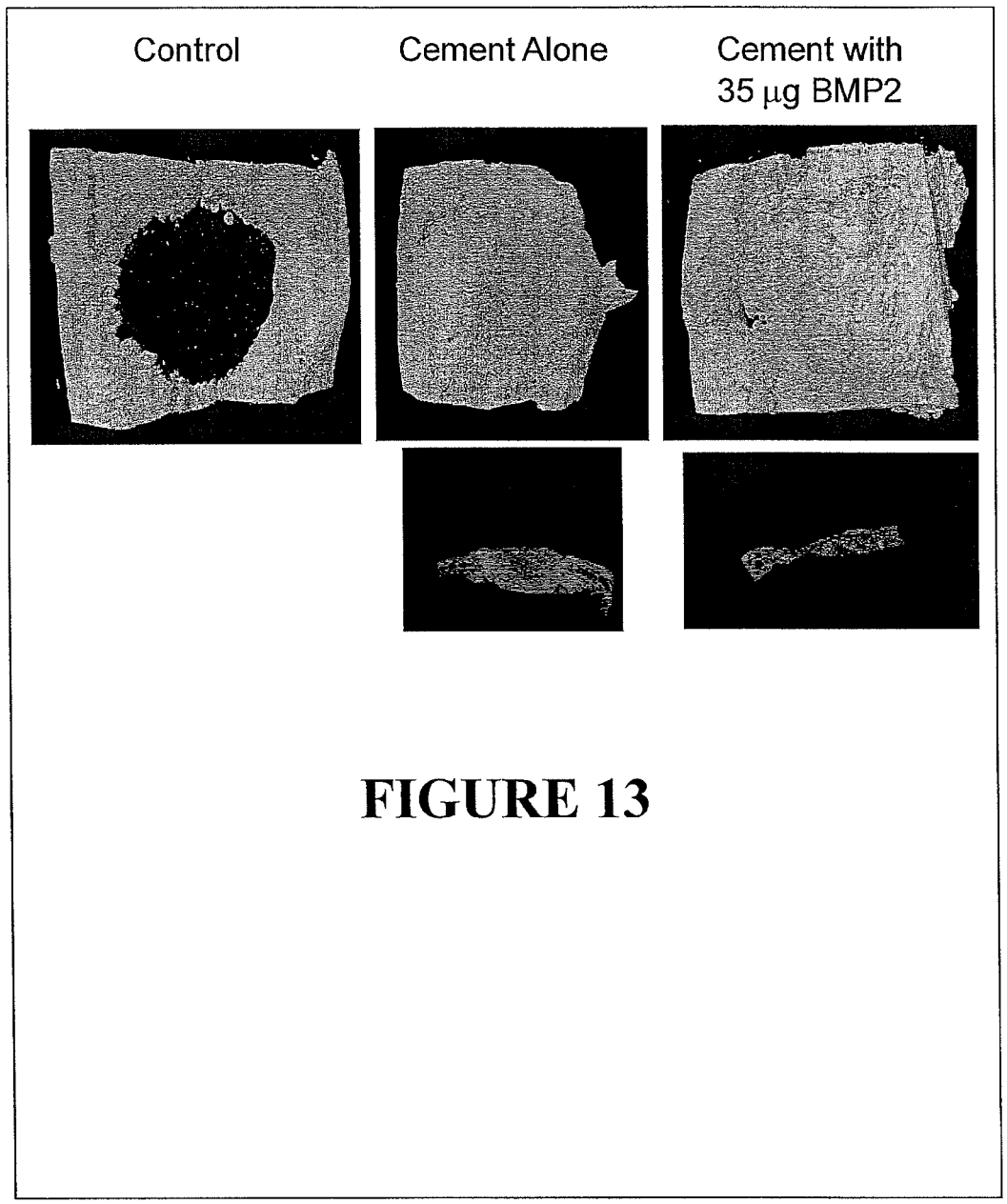
FIG. 13 is a micro-CT assessment (photographs) showing a comparison of a known composition with bone substitute compositions in accordance with embodiments of the present invention.

Post implant 8 weeks in vivo results on PCC-CPC without BMP-2 scaffolds implanted in an ulnae and craniofacial critical size defect model using radiographical, micro-CT and histological assessment (FIGS. 10 and 13) demonstrated the formation of new bone on the surface and bulk of the porous scaffold thus indicating rapid dissolution of the cement.

Cement with rhBMP-2 Results

Figures 11A, 11B:
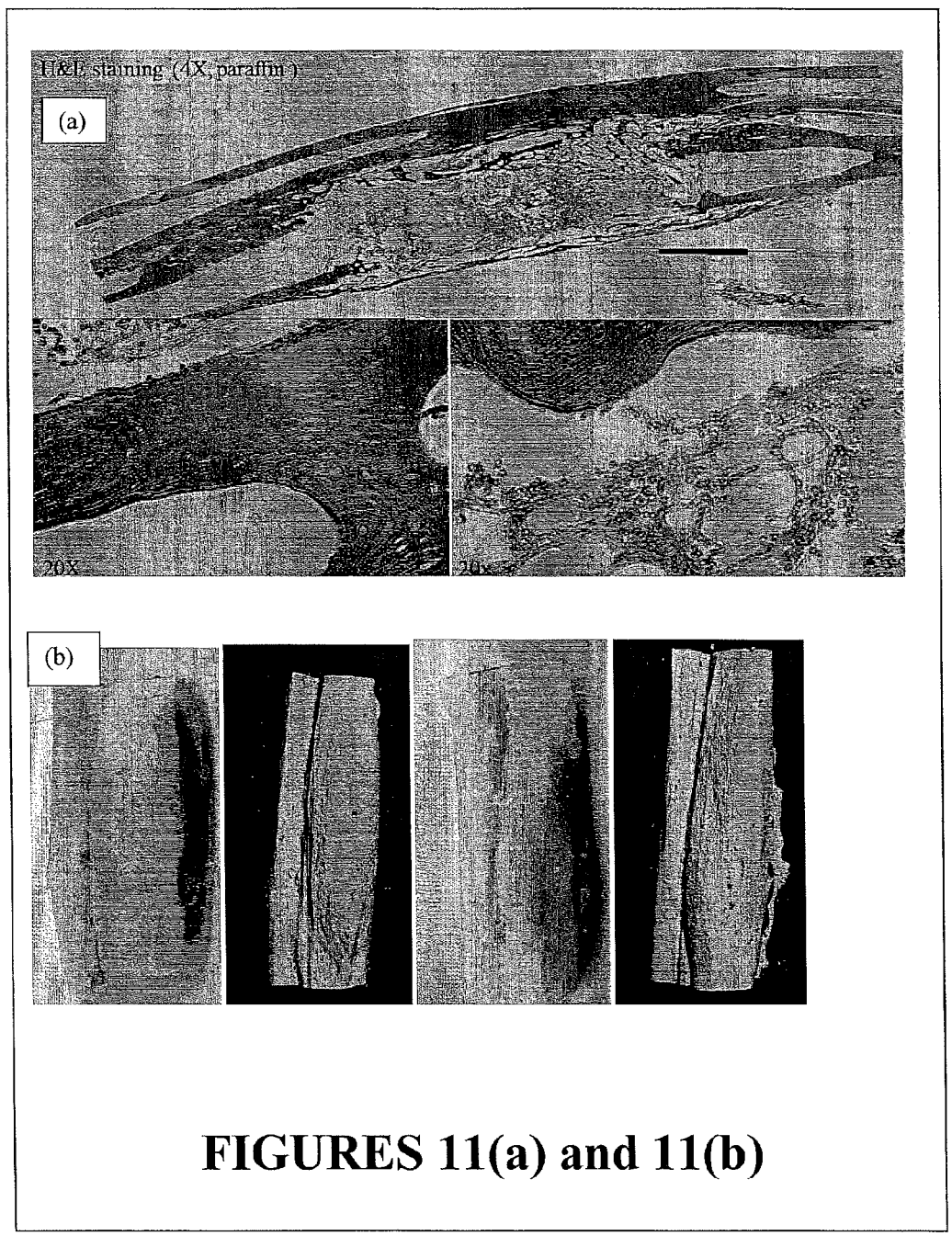
FIG. 11(a) is a histological assessment showing new bone formation for a bone substitute composition in accordance with an embodiment of the present invention.
FIG. 11(b) is a micro-CT and picture showing an explant and implant of a bone substitute compositions in accordance with an embodiment of the present invention.
Figure 11C:
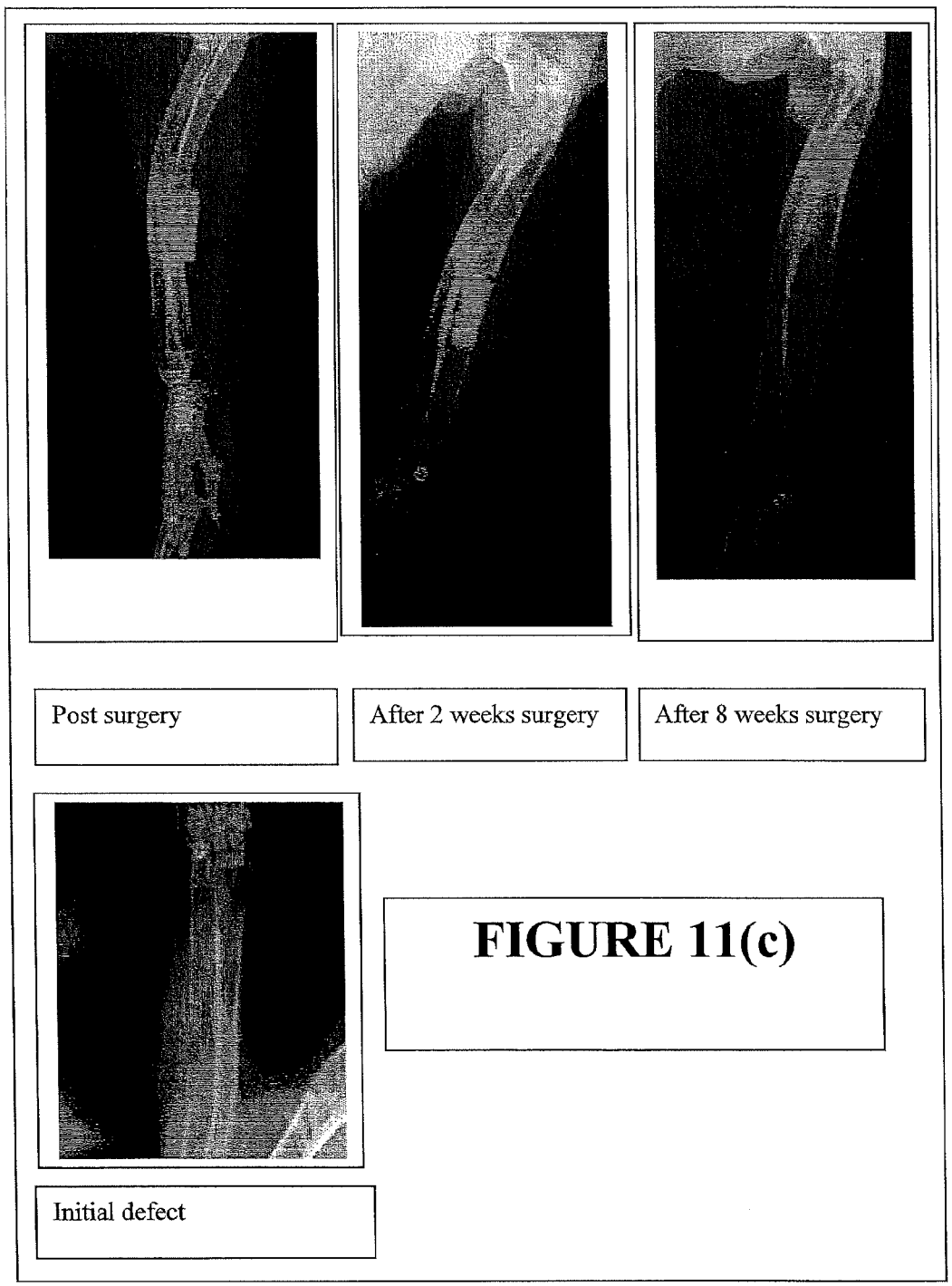
FIG. 11(c) is a radiography of an implanted bone substitute composition in accordance with an embodiment of the present invention.

FIG. 11(c) shows the radiographic images of the ulnae immediately following post surgery, after 2 weeks and after 8 weeks. The radiograph after 8 weeks shows complete resorption of the cement with the formation of new bone filling the original defect shown in FIG. 11(c). MicroCT analysis (FIGS. 11 and 13) in both the ulnae and calvarial bones show full bone regeneration and bridging of the defect with bone as shown by histological analysis (FIG. 11(a)).

Figure 9:
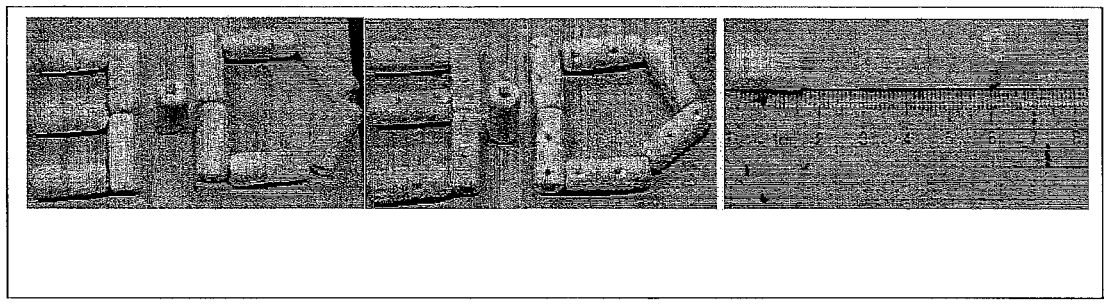
FIG. 9 is a digital image showing printed scaffolds of a bone substitute composition in accordance with an embodiment of the invention.
Figure 12:
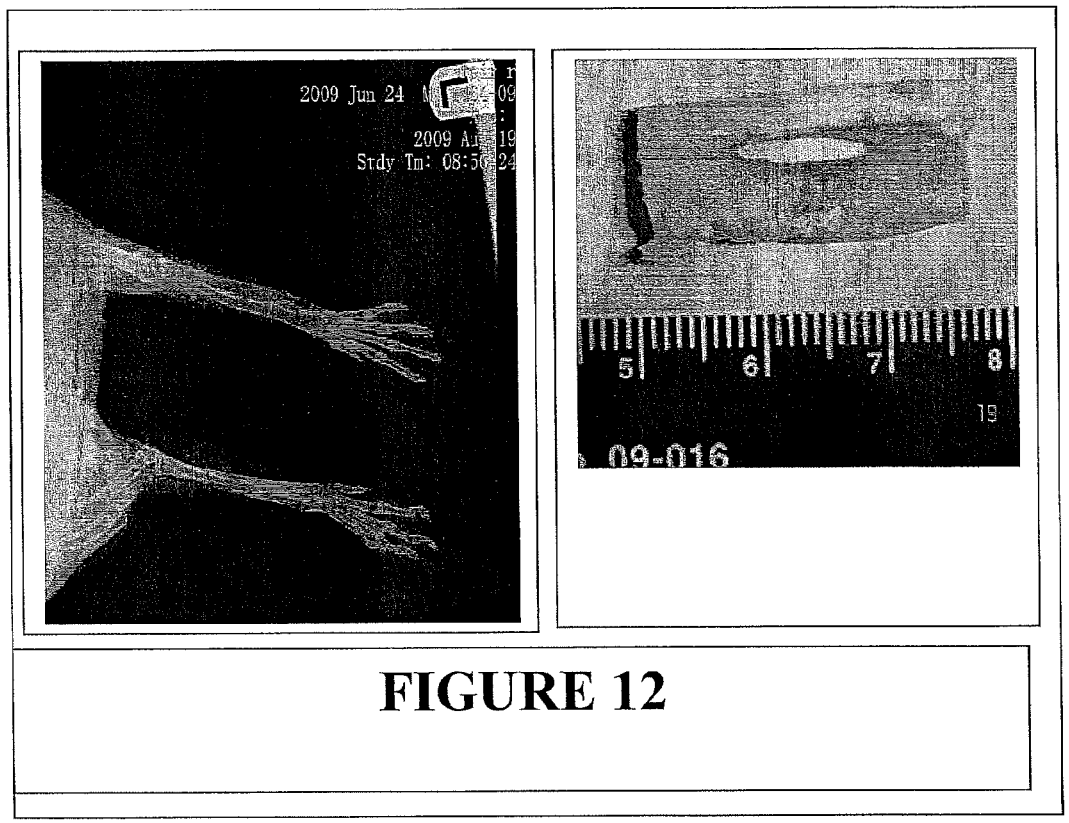
FIG. 12 is a x-ray radiograph showing an implant and a picture showing the retrieved implant of a bone substitute composition in accordance with an embodiment of the present invention.

FIG. 12 shows the radiograph of the ulna following 8 weeks of surgical implantation of the 3-D printed scaffold structures as described and shown in FIG. 9. The results show the closure of the non-union.

The Subcutaneous cement implantation results demonstrated that the cement is osteo-inductive. FIG. 14 shows an H&E staining of the decalcified cement implant infiltrated by cells from the adjacent wound area. The cells have deposited an extracellular matrix that can be visualized by the H&E stain. This matrix already at 4 weeks post-implantation contains bone specific proteins such as bone sialoproteins (BSP) as shown by immunohistochemistry staining using an ani-BSP antibody (FIG. 14).

Whereas particular embodiments of the invention have been described herein for purposes of illustration, it will be evident to those skilled in the art that numerous variations of the details may be made without departing from the invention as set forth in the appended claims.

What is claimed is:

1. A method of preparing a bone substitute material, comprising:
   combining calcium phosphate, acidic calcium salt, basic calcium salt, material selected from the group consisting of monosodium hydrogen phosphate, disodium hydrogen phosphate and mixtures thereof, and porogen to form a powder component; and
   mixing the powder component with a liquid colloidal mixture comprising nanoparticulate calcium phosphate and calcium salt, the colloidal mixture being complexed with at least one of a compound selected from the group consisting of protein, peptide, DNA, drug, stem cell, normal cell, and combinations thereof,
   wherein the bone substitute material is effective to regenerate bone in the absence of a biological growth component.

2. The method of claim 1, wherein the nanoparticulate calcium phosphate is formed by reacting calcium and non-acidic ionic phosphate.

3. The method of claim 2, wherein the reacting step is carried out in the presence of hydroxyl ions.

4. The method of claim 3, wherein the calcium ions are present in excess in the reaction as compared to phosphate ions.

5. The method of claim 3, wherein the hydroxyl ions comprise hydroxide material selected from the group consisting of sodium hydroxide, potassium hydroxide, ammonium hydroxide, tetraalkyl ammonium hydroxide, and mixtures thereof.

6. The method of claim 2, wherein the non-acidic ionic phosphate is selected from the group consisting of trisodium phosphate, tripotassium phosphate, tris(tetra-alkyl)ammonium phosphate.

7. The method of claim 2, wherein the reacting step further includes the presence of a buffer.

8. The method of claim 1, further comprising adding plasticizer to at least one of the powder component and the liquid colloidal mixture.

9. The method of claim 1, wherein the calcium phosphate is selected from the group consisting of monocalcium monophosphate anhydrite, calcium hydrogenphosphate dihydrate, calcium hydrogenphosphate anhydrite, hydroxyapatite, alpha-tricalcium phosphate, beta-tricalcium phosphate, fluorapatite, octacalcium phosphate, tetracalcium phosphate, carbonated calcium phosphate and mixtures thereof.

10. The method of claim 1, wherein the acidic calcium salt is selected from the group consisting of calcium sulfate, calcium hydrogenphosphate dihydrate, calcium hydrogenphosphate anhydrite, calcium oxalate, calcium citrate, calcium tartrate, calcium picrate and mixtures thereof.

11. The method of claim 1, wherein the basic calcium salt is selected from the group consisting of calcium carbonate, calcium bicarbonate, calcium dihydroxide, and mixtures thereof.

12. The method of claim 1, wherein the porogen is selected from the group consisting of recrystallized organic salt, recrystallized inorganic salt, engineered peptide, natural polymer, a composite of natural and synthetic polymers, synthetic biodegradable polymer, natural extra cellular matrix protein, and mixtures thereof.

13. The method of claim 1, further comprising complexing the colloidal mixture with at least one of a compound selected from the group consisting of protein, peptide, DNA, drug, stem cell, normal cell, and combinations thereof.

14. The method of claim 1, wherein the porogen is present in an amount such that the bone substitute material has a porosity of about 80 percent or greater.

* * * * *

UNITED STATES PATENT AND TRADEMARK OFFICE
CERTIFICATE OF CORRECTION

PATENT NO. : 8,557,235 B2  
APPLICATION NO. : 13/711261  
DATED : October 15, 2013  
INVENTOR(S) : Prashant Nagesh Kumta et al.

It is certified that error appears in the above-identified patent and that said Letters Patent is hereby corrected as shown below:

Title page, first column, (73) Assignee:, "University of Pittsburgh-Of the Commonwealth System of Hihger Education, Pittsburgh, PA (US)" should read --University of Pittsburgh-Of the Commonwealth System of Higher Education, Pittsburgh, PA (US)--.

In the Specification  
Column 8, line 3, "2.33 Wee" should read --2.33 g/cc--.

Signed and Sealed this  
Sixth Day of May, 2014

Michelle K. Lee  
*Deputy Director of the United States Patent and Trademark Office*